(12) United States Patent
Talghader

(10) Patent No.: US 7,800,066 B2
(45) Date of Patent: Sep. 21, 2010

(54) DETECTION BEYOND THE STANDARD RADIATION NOISE LIMIT USING REDUCED EMISSIVITY AND OPTICAL CAVITY COUPLING

(75) Inventor: Joseph J. Talghader, Edina, MN (US)

(73) Assignee: Regents of the University of Minnesota Office for Technology Commercialization, St. Paul, MN (US)

( * ) Notice: Subject to any disclaimer, the term of this patent is extended or adjusted under 35 U.S.C. 154(b) by 0 days.

(21) Appl. No.: 11/999,739

(22) Filed: Dec. 6, 2007

(65) Prior Publication Data

US 2008/0217539 A1    Sep. 11, 2008

Related U.S. Application Data

(60) Provisional application No. 60/873,650, filed on Dec. 8, 2006.

(51) Int. Cl.
*G01J 5/20*    (2006.01)
(52) U.S. Cl. .................. 250/338.1; 250/339.01
(58) Field of Classification Search ............ 250/338.1, 250/338.4, 339.11, 339.12
See application file for complete search history.

(56) References Cited

U.S. PATENT DOCUMENTS

| | | | |
|---|---|---|---|
| 5,021,663 A | 6/1991 | Hornbeck | |
| 5,142,414 A | 8/1992 | Koehler | |
| 5,286,976 A | 2/1994 | Cole | |
| 5,367,167 A | 11/1994 | Keenan | |
| 5,550,373 A | 8/1996 | Cole et al. | |
| 5,589,689 A | 12/1996 | Koskinen | |

(Continued)

FOREIGN PATENT DOCUMENTS

DE    43 34 578    4/1995

(Continued)

OTHER PUBLICATIONS

Aratani et al., "Micro Electro Mechanical Systems, An Investigation of Micro Structures, Sensors, Actuators, Machines and Systems," Sponsored by the IEEE Robotics and Automation Society in cooperation with the ASME Dynamic Systems and Control Division, "Process and Design Considerations for Surface Micromachined Beams for A Tuneable Interferometer Array in Silicon," 1993, pp. 230-235.

(Continued)

*Primary Examiner*—David P Porta
*Assistant Examiner*—Yara B Green
(74) *Attorney, Agent, or Firm*—Kagan Binder, PLLC

(57) ABSTRACT

The present invention provides thermal detectors having an optical cavity that is optimized to couple light into a sensor. Light that is on resonance is coupled with the sensor with as high as 100% efficiency, while light off resonance is substantially reflected away. Light that strikes the sensor from the sides (i.e. not on the optical cavity axis) only interacts minimally with sensor because of the reduced absorption characteristics of the sensor. Narrowband sensors in accordance with the present invention can gain as much as 100% of the signal from one direction and spectral band, while receiving only a fraction of the normal radiation noise, which originates from all spectral bands and directions.

30 Claims, 16 Drawing Sheets

U.S. PATENT DOCUMENTS

| | | | |
|---|---|---|---|
| 5,629,521 | A | 5/1997 | Lee et al. |
| 5,688,699 | A | 11/1997 | Cunningham et al. |
| 6,097,031 | A * | 8/2000 | Cole .................... 250/370.06 |
| 6,133,572 | A | 10/2000 | Cunningham |
| 6,222,454 | B1 | 4/2001 | Harling et al. |
| 6,262,417 | B1 * | 7/2001 | Ju ............................ 250/338.1 |
| 6,303,934 | B1 | 10/2001 | Daly et al. |
| 6,339,493 | B1 | 1/2002 | Scalora et al. |
| 6,518,597 | B1 | 2/2003 | Kim |
| 6,534,977 | B1 | 3/2003 | Duncan et al. |
| 6,573,504 | B2 | 6/2003 | Iida et al. |
| 6,608,711 | B2 | 8/2003 | Flanders et al. |
| 6,618,199 | B2 | 9/2003 | Cook |
| 6,667,479 | B2 | 12/2003 | Ray |
| 6,791,736 | B2 | 9/2004 | Jain |
| 6,806,470 | B2 | 10/2004 | Iida et al. |
| 6,816,636 | B2 | 11/2004 | Cole et al. |
| 6,900,440 | B2 | 5/2005 | Reed et al. |
| 7,002,697 | B2 | 2/2006 | Domash et al. |
| 7,015,457 | B2 | 3/2006 | Cole et al. |
| 7,095,026 | B2 | 8/2006 | Devitt et al. |
| 7,145,143 | B2 | 12/2006 | Wood et al. |
| 7,196,790 | B2 | 3/2007 | Cole |
| 7,262,413 | B2 | 8/2007 | Kauffman et al. |
| 7,460,246 | B2 | 12/2008 | Kothari |
| 2002/0040967 | A1 | 4/2002 | Oda |
| 2003/0072009 | A1 * | 4/2003 | Domash et al. ............. 356/519 |
| 2004/0089807 | A1 | 5/2004 | Wada et al. |
| 2004/0200962 | A1 | 10/2004 | Ishikawa et al. |
| 2004/0202399 | A1 | 10/2004 | Kochergin et al. |
| 2004/0217264 | A1 | 11/2004 | Wood et al. |
| 2004/0218509 | A1 | 11/2004 | Flanders et al. |
| 2005/0017177 | A1 | 1/2005 | Tai et al. |
| 2005/0226281 | A1 | 10/2005 | Faraone et al. |
| 2006/0039009 | A1 | 2/2006 | Kiesel et al. |
| 2006/0077528 | A1 | 4/2006 | Floyd |
| 2006/0091284 | A1 | 5/2006 | Viens et al. |
| 2007/0215808 | A1 | 9/2007 | Sekiguchi et al. |
| 2008/0035846 | A1 | 2/2008 | Talghader et al. |
| 2009/0140144 | A1 | 6/2009 | Myrick et al. |

FOREIGN PATENT DOCUMENTS

| | | |
|---|---|---|
| EP | 0 608 049 | 7/1994 |
| GB | 2 231 713 | 11/1990 |
| JP | 2005156255 | 6/2005 |
| WO | WO 96/21140 | 7/1996 |
| WO | WO 01/81879 | 11/2001 |
| WO | WO 2004/015783 | 2/2004 |
| WO | WO 2005/003704 | 1/2005 |
| WO | WO 2005/022900 | 3/2005 |

OTHER PUBLICATIONS

IBM Technical Disclosure Bulletin, vol. 32, No. 8A, Jan. 1990, 4 pages.

Aratani et al., "Surface Micromachined Tuneable Interferometer Array," Sensors and Actuators A, 43 (1994) pp. 17-23.

Neikirk et al., "Design of Infrared Wavelength-Selective Microbolometers Using Planar Multimode Detectors," Microelectronics Research Center, The University of Texas at Austin, SPIE's Microtechnologies for the New Millennium, 15-18, May 2003, pp. 1-16.

Li et al., "Thermal simulation of micromachines bridge and self-heating for uncooled $VO_2$ infrared microbolometer," Sensors and Actuators ! 126 (2006) pp. 430-435.

Theocharous et al., "Detectors for Mid- and Far-infrared Spectrometry: Selection and Use," Instrumentation for Mid- and Far-infrared Spectroscopy, John Wiley & Sons Ltd., (2002), pp. 349-367.

Wang et al., "Step-Wise Tunable Microbolometer Long-Wavelength Infrared Filter," Electrical and Computer Engineering, University of Minnesota, 4 pages, Jun. 5, 2005.

A.S. Welling et al., "Antenna-coupled microbolometers for multi-spectral infrared imaging," Proceedings of the SPIE, vol. 6206, pp. 62061F-1 to 62061F-8, 2006.

S. Han et al., "Multilayer fabry-perot microbolometers for infrared wavelength selective detectors," Proceedings of the SPIE, vol. 6206, pp. 62061G-1 to 62061G-7, 2006.

V.N. Leonov et al., "Two-color thermal detector with thermal chopping for infrared focal plane arrays," Applied Optics, vol. 40, No. 16, 2001.

M. Almasri et al., "Amorphous silicon two-color microbolometer for uncooled IR detection," IEEE Sensors Journal, vol. 6, No. 2, pp. 293-300, 2006.

Talghader et al., U.S. Appl. No. 11/805,240, filed May 22, 2007.

* cited by examiner

| Layer | Material | Thick A | n | k |
|---|---|---|---|---|
| 1 | Ge | 6062 | 4 | 0 |
| 2 | SrF2 | 17321 | 1.4 | 0 |
| 3 | Ge | 6062 | 4 | 0 |
| 4 | Air | 24250 | 1 | 0 |
| 5 | ZnS_doped | 500 | 2.2 | 0.05 optimal |
| 6 | Air | 24250 | 1 | 0 |
| 7 | Ge | 6062 | 4 | 0 |
| 8 | SrF2 | 17321 | 1.4 | 0 |
| 9 | Ge | 6062 | 4 | 0 |
| 10 | SrF2 | 17321 | 1.4 | 0 |
| 11 | Ge | 6062 | 4 | 0 |
| 12 | SrF2 | 17321 | 1.4 | 0 |
| 13 | Ge | 6062 | 4 | 0 |
| 14 | SrF2 | 17321 | 1.4 | 0 |
| 15 | Ge | 6062 | 4 | 0 |

| Thickness (microns) | n | k | Structure |
|---|---|---|---|
| .606 | 4 | 0 | Mirror layer |
| 1.732 | 1.4 | 0 | Mirror layer |
| .606 | 4 | 0 | Mirror layer |
| 2.425 | 1 | 0 | Gap |
| .0500 | 2.2 | .05 | Sensor |
| 2.425 | 1 | 0 | Gap |
| .606 | 4 | 0 | Mirror layer |
| 1.732 | 1.4 | 0 | Mirror layer |
| .606 | 4 | 0 | Mirror layer |
| 1.732 | 1.4 | 0 | Mirror layer |
| .606 | 4 | 0 | Mirror layer |
| 1.732 | 1.4 | 0 | Mirror layer |
| .606 | 4 | 0 | Mirror layer |
| 1.732 | 1.4 | 0 | Mirror layer |
| .606 | 4 | 0 | Mirror layer |

Fig. 4

| Thickness (microns) | n | k | Structure |
|---|---|---|---|
| .606 | 4 | 0 | Mirror layer |
| 1.732 | 1.4 | 0 | Mirror layer |
| .606 | 4 | 0 | Mirror layer |
| 4.700 | 1 | 0 | Gap |
| .050 | 2.2 | 3 | Sensor |
| .200 | 1 | 0 | Gap |
| .606 | 4 | 0 | Mirror layer |
| 1.732 | 1.4 | 0 | Mirror layer |
| .606 | 4 | 0 | Mirror layer |
| 1.732 | 1.4 | 0 | Mirror layer |
| .606 | 4 | 0 | Mirror layer |
| 1.732 | 1.4 | 0 | Mirror layer |
| .606 | 4 | 0 | Mirror layer |
| 1.732 | 1.4 | 0 | Mirror layer |
| .606 | 4 | 0 | Mirror layer |

Fig. 19

DETECTION BEYOND THE STANDARD RADIATION NOISE LIMIT USING REDUCED EMISSIVITY AND OPTICAL CAVITY COUPLING

CROSS-REFERENCE TO RELATED APPLICATION

The present application claims priority to U.S. Provisional Application No. 60/873,650, filed Dec. 8, 2006, the entire contents of which are incorporated herein by reference for all purposes.

GOVERNMENT RIGHTS

This invention was made with Government support under Grant No. DAAD19-03-1-0343, awarded by the Army Research Office.

TECHNICAL FIELD

The present invention is directed to infrared detectors and related methods. In particular, the present invention is directed to high sensitivity uncooled thermal detectors that function with noise floors below the standard blackbody radiation limit. Thermal detectors in accordance with the present invention include microbolometers based detectors as well as ferroelectric, pyroelectric, and thermoelectric detectors. The techniques described herein can also benefit photon (e.g., p-n junctions and photoconductors) based detectors under certain conditions.

BACKGROUND

Thermal detectors include a sensor that absorbs light energy and then transduces the resulting heat into a useful electrical signal related to the amount or type of light absorbed. Perhaps the most prominent current thermal detectors include microbolometers, which absorb light across a broad band of the infrared, usually the mid-wave infrared (MWIR, corresponding to wavelengths of roughly 3 microns to 5 microns) or long wave infrared (LWIR, roughly 8 microns to 14 microns) and then convert heat into a change in resistance. These devices are very popular in commercial uncooled imaging cameras. Their basic structure includes a small micromachined sensor plate connected to an underlying substrate by thin support beams. The support beams have a low thermal conductance so that large increases in the temperature of the sensor plate occur with small amounts of absorbed light. The sensor plate includes a resistor made of a material with a high magnitude temperature coefficient of resistance (TCR). One common TCR material in use is vanadium oxide, originally developed for microbolometers in the 1980's. A pulsed or continuous bias current is applied to the resistor and the absorbed light energy can be measured through the voltage response. Some other common thermal detector technologies include thermoelectric detectors where the heat from light is converted into a voltage using the Seebeck effect, and pyroelectric detectors where heat from absorbed light induces a voltage signal via a change in the internal polarization of a ferroelectric material.

There are a variety of noise sources that can limit the performance of a thermal detector. For a biased single-pixel detector, the most important of these include Johnson noise, 1/f noise, and thermal noise. Thermal noise originates from the fluctuations in the quanta of energy transferred to and from the detector. These quanta can take the form of either phonons if solid-state conduction dominates the heat transfer or photons if radiation dominates. Traditionally, radiation heat transfer has been considered the fundamental noise limit because even if all of the other noise sources are reduced by technological innovations, the photon fluctuations still remain due to Planck's Law.

Current broadband thermal detector devices are beginning to perform in regimes where radiation noise must be considered. An example of this is shown in U.S. Publication Nos. 2002/0139933 and 2001/0028035 which describe a microbolometer with low thermal conductance supports. In one embodiment, the authors propose to select a material for the backside of their detector which has a radiation emission lower than many other materials.

The radiation limit is more forgiving than has been previously considered. Because radiation heat transfer is directly proportional to emissivity and emissivity is identical to absorption through Kirchoff's Law, a low absorption structure will interact with the radiation of the background much less than a normal thermal detector, which is usually optimized for high absorption. For a typical detector, this does nothing to improve performance because the received optical signal is reduced by the same amount. If the signal light can be coupled into the sensor of the detector at near 100% efficiency while maintaining a low absorption for the rest of the background, then the traditional thermal radiation noise could be reduced by multiple orders of magnitude.

Most thermal detectors operate with broad bands. Many current devices have a reflector beneath them to allow light transmitted through the device another chance to be absorbed. The gaps between the bolometer and substrate in these structures are roughly a quarter-wave length to enhance coupling across a wide band. In a sense, the entire bolometer plus substrate can be though of as a highly absorbing distributed "mirror." A variety of narrowband detectors using integrated external etalons have been proposed, perhaps the most advanced of which are described by in U.S. Pat. Nos. 7,015,457 and 5,550,373 to Cole et al. A multispectral bolometer concept that uses scattering rather than interference to distribute different wavelengths is described in U.S. Pat. No. 5,629,521 to Lee et al. Detectors with integrated filtering are described in U.S. Pat. No. 5,589,689 to Koskinen, U.S. Publication No. 2005/0017177 to Tai et al., and U.S. patent application Ser. No. 11/805,240 to Talghader et al.

SUMMARY

The present invention provides high sensitivity thermal detectors that perform far beyond the blackbody radiation noise limit. Thermal detectors in accordance with the present invention comprise a low emissivity (absorption) sensor such as a microbolometer plate, for example, positioned within an optical cavity. The optical cavity is at least partially defined by thin-film mirror structures. The absorption of the sensor is preferably matched to the reflectivity of the cavity mirrors thereby optimizing coupling of radiation with the sensor. Curvature of the mirrors is also preferably optimized to minimize the area of the sensor while maximizing the amount of radiation collected by the sensor. Radiation that is on resonance is coupled with the sensor at as high as 100% efficiency, while radiation off resonance is reflected away. Advantageously, radiation that strikes the sensor from the sides (i.e. not on the optical cavity axis) only interacts minimally with the sensor because of the reduced absorption characteristics of the sensor. Narrowband thermal detectors in accordance with the present invention can gain as much as 100% of the signal from one direction and spectral band, while receiving only a fraction of the normal radiation noise, which originates from all spectral bands and directions.

Thermal detectors in accordance with the present invention have a noise floor below the broadband thermal radiation limit. For current state of the art microbolometer based thermal detectors, typical noise powers for thermal radiation noise vary from picowatts to tens of picowatts depending on the area of the detector. Area for area, microbolometer based thermal detectors in accordance with the present invention achieve noise powers an order of magnitude better than the state of the art detectors.

Thermal detectors in accordance with the present invention also preferably utilize ultra-low thermal conductance support structures and provide sub-radiation limit sensitivity for large area devices or small single pixels. In one embodiment supports comprising a dielectric structural layer and conductor are preferably used. In the current state of the art, these supports can have thermal conductances on the order of $10^{-9}$ W/K with resistances on the order of 100 k$\Omega$ or less. In general, when using the same materials, a higher thermal conductance leads to a lower electrical resistance. Some preferred support materials include low thermal conductivity dielectrics such as silicon dioxide and magnetic metal alloys such as nickel-iron (NiFe), for example. For detectors using continuous bias read-out and similar read-outs with low Johnson and 1/f noise, low thermal conductivity support structures can be used to achieve sensitivity beyond the standard blackbody radiation limit. However, to obtain array compatible small pixels at maximum sensitivity using pulse bias read-out, more advanced support structures such those using thermal switching and/or interface contacts are preferably used. Sensitive read-outs may use optical means, say by tracking the spectral position of the cavity optical resonance or the spatial position of the pattern diffracted, transmitted, refracted, or reflected from the sensor by a read-out optical probe. While optical techniques are more difficult with imaging arrays, such techniques have the advantage of reducing or eliminating electrical read-out noise.

Sensors in accordance with the present invention preferably comprise thin membranes, not only for emissivity reasons, but also for optimizing time constant. In order to operate in the thermal radiation limit, the thermal conductance must be extremely low, which forces the time constant of the sensors to undesirably high values. To circumvent this, sensor membranes are preferably reduced in thickness to a few tens of nanometers or less. In this way, typical frame rate detection can still be achieved. It should be noted that having long time constants in some potential applications such as chemical sensing or astronomy is not necessarily detrimental, so the exact thickness desired will be a function of desired time constant, sensor area, and materials used.

Exemplary sensor materials comprise $VO_x$ and $SiO_2$. $VO_x$ is one of the industry standard TCR materials, having been used since at least the mid-80's in microbolometers, and as a result has a well-characterized high-TCR response. The $SiO_2$ is used as an etch stop and structural material. $VO_x$ can be deposited to have minimal absorption in the LWIR, and $SiO_2$, with a strong absorption near 10 microns, can be deposited to a thickness chosen to give a desired emissivity near that wavelength. Other materials can be used for other wavelengths or for wavelength-tunable devices. For example, a thin metal can be used in an absorber if a tunable device were desired, because metals commonly have a more uniform spectral absorption across the LWIR or MWIR as compared to $SiO_2$ and therefore would couple properly to an entire range of optical cavity resonances. For the supports, materials having low thermal conductivity and conductive layers with a high ratio of electrical to thermal conductivity are preferred. Exemplary materials include silicon dioxide as the structural support material and sputtered NiFe as the conductor.

The present invention also provides pixel structures, for example, for imaging chemical lines at high sensitivity. Such pixel structures have a noise equivalent power (NEP) that is at least one order of magnitude lower than an equivalent state of the art microbolometer based detector due to the reduced interaction with the radiation background provided by detectors of the present invention.

Additionally, thermal detectors in accordance with the present invention can be made tunable by using an electrostatic actuator that controls the relative spacing of the mirrors and sensor.

In an aspect of the present invention, a thermal detector for sensing infrared radiation is provided. The thermal detector comprises a resonant optical cavity at least partially defined by first and second spaced apart layered thin-film mirror structures; and an infrared sensor operatively positioned between the first and second thin-film mirror structures and suspended within the resonant optical cavity by one or more electrically conductive support beams so radiation received by the resonant optical cavity impinges on at least a surface portion of the infrared sensor. The optical cavity may include plural sensors.

In another aspect of the present invention, a thermal detector for sensing infrared radiation is provided. The thermal detector comprises a resonant optical cavity at least partially defined by first and second spaced apart layered thin-film mirror structures; and an infrared sensor operatively positioned between the first and second thin-film mirror structures and suspended within the resonant optical cavity by one or more electrically conductive support beams so radiation received by the resonant optical cavity impinges on at least a portion of the infrared sensor and wherein said portion of the infrared sensor has an absorption less than or equal to twenty-five percent. Preferably, said portion of the infrared sensor has an absorption less than or equal to twenty-five percent in the range of about 8 microns to about 14 microns at room temperature. This wavelength range will move shorter at higher background temperatures.

In another aspect of the present invention, a method of sensing infrared radiation is provided. The method comprises the steps of providing a resonant optical cavity at least partially defined by first and second spaced apart mirror structures and an infrared sensor suspended within the resonant optical cavity; causing radiation to enter the resonant optical cavity and couple with the infrared sensor; and measuring a change in the infrared sensor caused by the radiation coupled with the infrared sensor.

In yet another aspect of the present invention, a method of making a thermal detector for sensing infrared radiation is provided. The method comprises the steps of forming a resonant optical cavity at least partially defined by first and second spaced apart thin-film mirror structures; suspending an infrared sensor within the resonant optical cavity; and positioning the infrared sensor within the optical cavity so the absorption of the resonant wavelength of the optical cavity by the sensor is greater than twenty-five percent.

BRIEF DESCRIPTION OF THE DRAWINGS

The accompanying drawings, which are incorporated in and constitute a part of this application, illustrate several aspects of the invention and together with description of the embodiments serve to explain the principles of the invention. A brief description of the drawings is as follows:

FIG. 4 is a table showing layer structure of a resonant optical cavity in accordance with the present invention having mirror structures comprising Ge/SrF$_2$. In this optical cavity structure, the sensor is centered within the optical cavity.

FIG. 19 is a table showing layer structure of a resonant optical cavity in accordance with the present invention having mirror structures comprising Ge/SrF$_2$. In this optical cavity structure, the sensor is not centered within the optical cavity.

DETAILED DESCRIPTION

Figure 1:
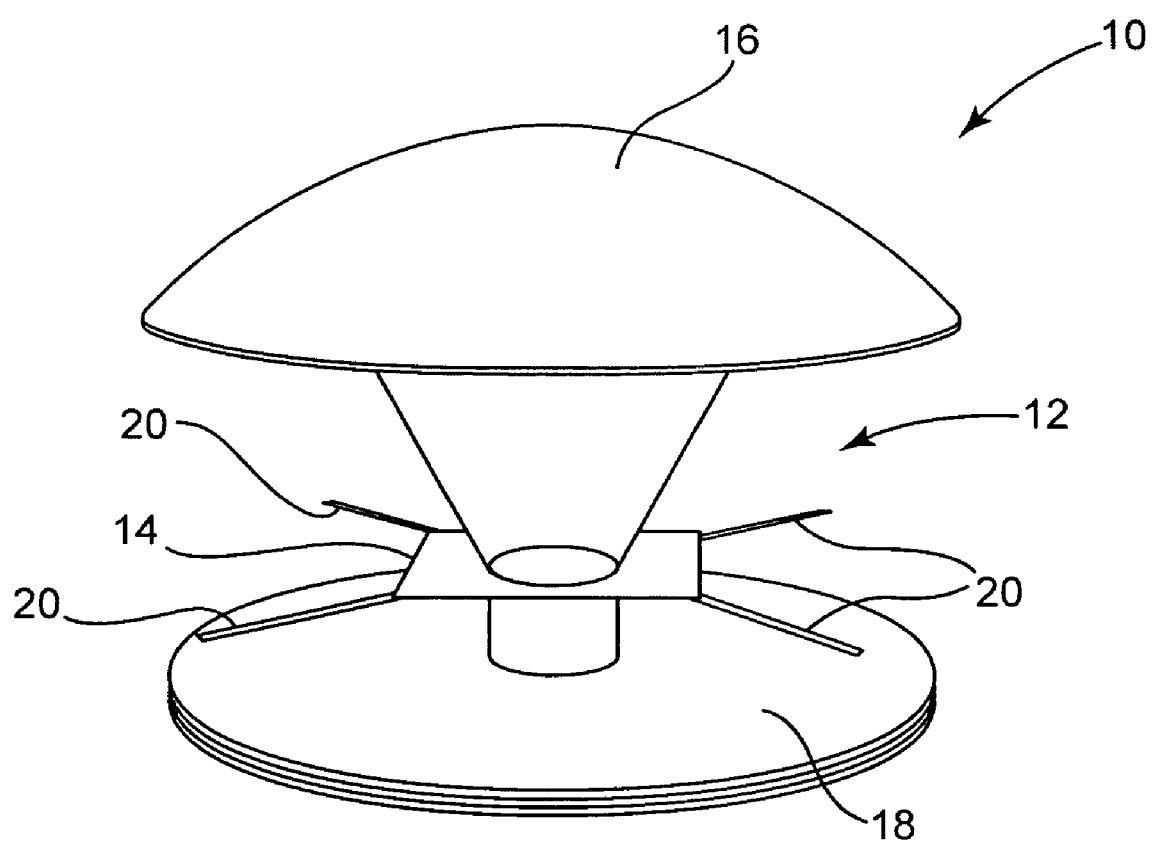
FIG. 1 is a schematic view of an exemplary ultra-high sensitivity narrowband thermal detector having a Gaussian optical cavity and a central absorbing sensor in accordance with the present invention. The sensor has low emissivity and therefore interacts strongest with radiation that is in the frequency band and direction of the optical cavity.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The radiation limit is widely known to dictate the ultimate performance of thermal detectors. Even if all other noise sources are eliminated or reduced to negligible levels, the transfer of photons between the detector, its surroundings, and the background will cause a minimum fluctuation in detected power. The present invention thus provides detectors having low enough emissivity (absorption) so that a sensor portion of the detector interacts only weakly with its surroundings. Normally, this is unacceptable because the sensor signal response decreases along with the noise. However, if the sensor is placed inside a properly matched optical cavity, then light in one direction and one frequency band will couple at 100% or near 100% to the sensor. Other wavelengths of radiation in the direction of the cavity axis will be rejected by the cavity, and radiation of any wavelength from other directions will interact only weakly with the low-absorption sensor element. With this type of device, the radiation noise limit can be dropped by two or more orders of magnitude, making narrowband uncooled detectors perform almost as well as the best cooled narrowband Indium Antimonide or Mercury Cadmium Telluride (MCT) photon detectors. The technology applies to both fixed-wavelength and tunable detectors. Tunable detectors are described in U.S. patent application Ser. No. 10/805,240 to Talghader et al., entitled "Tunable Finesse Infrared Cavity Thermal Detectors," and filed on 22 May 2007, the entire disclosure of which is incorporated by reference herein for all its entire disclosure and for all purposes.

Detection beyond the standard radiation noise limit can be extended to work at broader resonances to some degree; however, this process becomes less efficient the wider the band. To achieve broad response, the mirrors are made less reflective and the sensor more absorbing. These changes increase the interaction of the sensor with the background and reduce the ultimate performance of the device. In the trivial case, the performance enhancement decreases toward zero as one tries to cover the entire MWIR or LWIR. One can remove one mirror entirely and make the sensor highly absorbing to mimic architectures common to current microbolometers where a reflection from the substrate or other layer is used to couple extra radiation into the sensor (see U.S. Pat. Nos. 5,021,663 and 5,286,976 and U.S. Publication No. 2002/0179837, for example). Such devices have radiation noise near the traditional blackbody limit.

It is well known that two parallel mirrors separated by a multiple of a half wavelength will produce a Fabry-Perot optical cavity that has a transmission peak at that wavelength. The same interference phenomena that lead to high transmission can also be used to couple radiation into an absorbing layer in the resonant cavity. If a weakly absorbing layer is placed at a maximum of the field intensity inside a high Finesse cavity, then radiation on resonance will be strongly absorbed because it makes many passes through the absorber material. Radiation off resonance is rejected by the optical cavity itself and interacts little with the absorber.

As used herein the term optical cavity generally refers to a resonant Fabry-Perot-type interferometer comprising at least first and second mirror structures and the region between such mirror structures. The mirrors and the region between such mirrors may include absorbing, phase adjusting, sensing, and/or other layers in addition to reflecting layers. The region between such mirrors also preferably contains a vacuum but may comprise solid state layers such as used in photon detectors in accordance with the present invention. The optical cavities described herein comprise resonant optical cavities, that is, such optical cavities cause constructive interference on resonance within the optical cavity as opposed to destructive interference. This means that the optical cavity spacing between the mirror structures is approximately a multiple of a half wavelength of the resonant wavelength.

FIG. 1 schematically shows an exemplary device 10 in accordance with the present invention having a Gaussian optical cavity 12 and a central absorber 14 (sensor) between first and second mirror structures, 16 and 18, respectively.

Central absorber 14 is positioned in the optical cavity 12 by supports 20. As shown, mirror 16 comprises a curved structure and mirror 18 comprises a planar structure. Any desired mirror structure, however, can be used for mirrors 16 and 18 including curved and planar mirror structures. Mirror reflectivities that complement the absorption of the central layer are preferably used. As the sensor absorption decreases, the reflectivities of the mirrors must increase to insure that the requisite number of passes by the radiation is achieved. So a weaker absorber with properly designed mirrors means a sharper resonance.

Figures 2, 3:
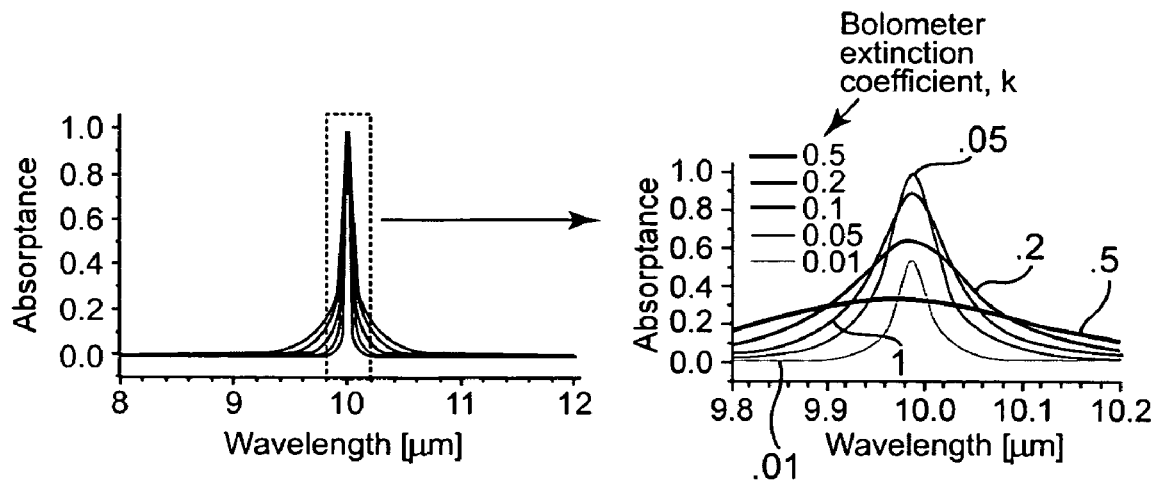
FIG. 2 is a table showing an exemplary layer structure and thicknesses for a cavity-enhanced absorption sensor in accordance with the present invention.
FIG. 3 is a graph showing absorbance versus wavelength for a sub-radiation-limit detector resonant optical cavity in accordance with the present invention having a layer structure similar to the layer structure of the table of FIG. 2.

FIG. 2 shows an exemplary layer structure for a long-wave infrared (LWIR) cavity that can be used with devices such as thermal detectors in accordance with the present invention. A simulated spectrum for the layer structure of FIG. 2 is shown in FIG. 3. The materials used in the exemplary mirrors are germanium and strontium fluoride while the central layer is zinc sulfide that has been doped to achieve a desired absorption of approximately 0.5% per pass. Such low absorptions are easy to achieve. One can either choose an absorbing material and make the material very thin or take a transparent material and dope the material with impurities until the desired level of absorption is achieved. As an example, a single layer of ZnS can be used as a sensor layer in accordance with the present invention, and functions as sensor, absorber, and structural material. Of course, these functions can be provided by plural layers.

One way to produce controlled absorption in a semiconductor (e.g. Ge or ZnS) that is normally transparent in the mid-wave infrared (3 to 5 microns) or long-wave infrared (8 to 14 microns) is to dope it. When this is done, phonons can mediate the interaction of free carriers with incident infrared photons. Because this process involves multiple entities, the resulting absorption coefficients are not as high as those of band-to-band transitions, but that is neither desirable nor necessary. The free-carrier absorption has a wavelength dependence $\alpha_{free} \sim \lambda^P$, where p is generally between 2 and 3 depending on which combination of acoustic phonons, optical phonons, or impurities mediate the interaction of carriers with light. The wavelength dependence produces a shift in coupling across the LWIR (or MWIR), but does not fundamentally alter performance if the system is optimized for the center of the desired band. Other useful layers that are intrinsically absorbing without doping include thin metals such as chromium or dielectrics such as silicon dioxide.

In accordance with the present invention an optical cavity with a weak absorbing layer positioned therein can be designed to couple essentially 100% of incident radiation into the absorber at one wavelength. The cavity rejects substantially all other radiation. However, this only relates to light along the direction of the optical cavity axis. Also important to the performance of a thermal detector, is how the radiation is absorbed in other directions. This directional effect can provide about a factor of 5 in performance enhancement for an f/4 system while spectral cavity characteristics (directionality and wavelength selectivity) provide about a factor of 20 for a standard chemical line, for a total of about a factor of 100. Because the absorbing layer can be made arbitrarily weak, about 1% or less, any radiation that is incident upon the absorber from directions other than the cavity axis will not have any additional round-trips of the system; therefore, off-axis radiation is absorbed at only very low levels. In other words, absorption is reduced for all directions and wavelengths except the specific direction and spectral band that the optical cavity is designed for.

Figure 6:
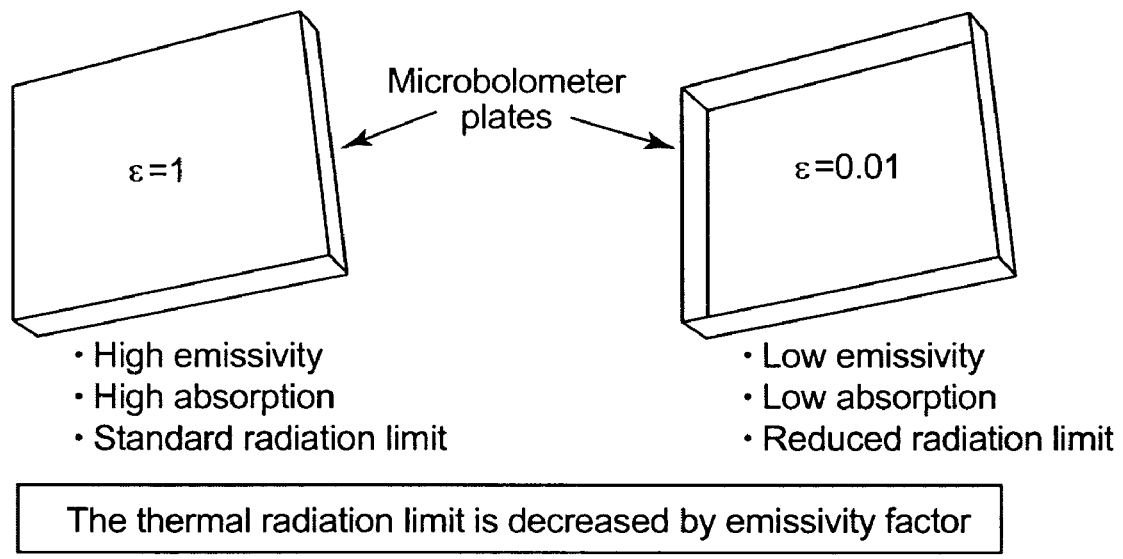
FIG. 6 is a conceptual diagram of the change in emissivity and absorptivity that results from a mostly transparent object.

The Stefan-Boltzmann radiation power equation for a thermal emitter is:

$$P_{rad} = 2A \in \sigma T^4$$

where A is the area of an element (the factor of two includes top and bottom), $\in$ is the emissivity, $\sigma$ is the Stefan-Boltzmann constant, and T is the temperature. The radiated power is directly proportional to the emissivity. Because absorptivity is equal to the emissivity by Kirchoff's Law, a hypothetical object that is transparent at all wavelengths will not emit any thermal radiation regardless of how hot it is. On the other hand, a weakly absorbing material will emit some thermal radiation, and a strongly absorbing material will emit as a blackbody with $\in \sim 1$ as shown in FIG. 6. According to Kirchoff's Law, any variations in the absorption of an object as a function of wavelength, polarization, or direction will also be carried over into the emission of that object. So fundamental physical law states that a system that absorbs in only one wavelength band in one range of directions will only emit radiation in that same band and direction.

Figure 5:
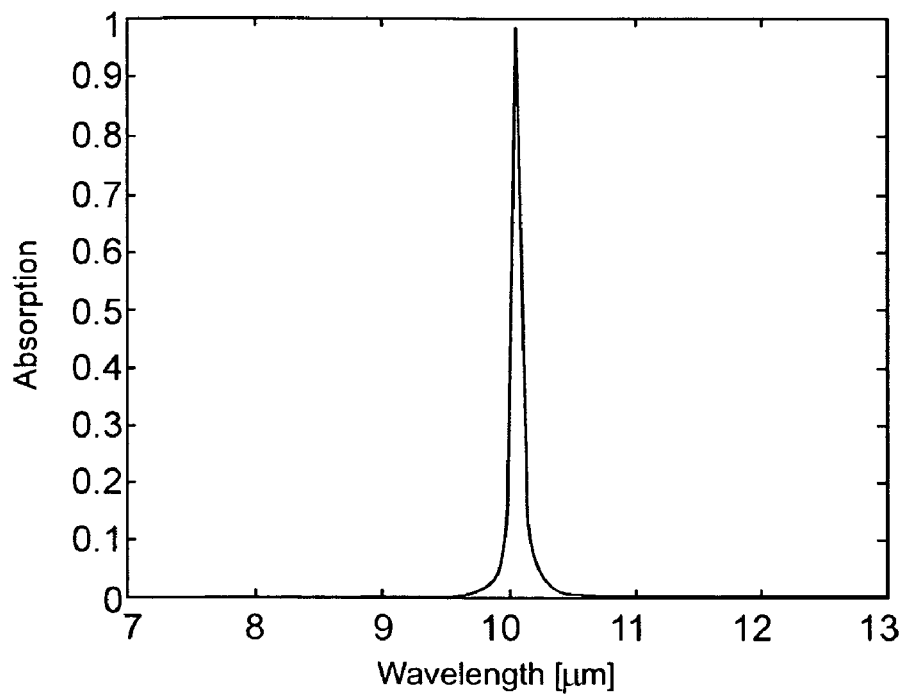
FIG. 5 is a graph of absorption versus wavelength for the resonant optical cavity of the table of FIG. 4.

The concept of low absorption and emissivity is not solely a function of the sensor structure itself but also is an aspect of the optical cavity and the sensor position within the optical cavity. A straightforward example can explain this. FIG. 4 shows the layer structure of a Fabry-Perot cavity with mirrors comprising Ge/SrF2 multilayers. The cavity is designed for a resonance near 10 microns and the mirrors are separated by a half-wavelength. The mirrors have high reflectivity but the bottom mirror reflectivity is nearly 100%. The central layers of the cavity include the innermost high index Ge layers from the mirrors and the low index vacuum (ignoring the ZnS sensor layer for the moment). Light at the resonant wavelength inside the optical cavity will form a standing wave with an intensity maximum in the center of the optical cavity (gap between mirror structures). A low-high-low index profile for the central layers would produce an intensity minimum in the center. Therefore, the radiation will have excellent coupling with any sensor centered in the optical cavity and only a low value of absorption is needed to couple most of the radiation into the sensor while rejecting off-resonance wavelengths. This is illustrated in FIG. 5 with a plot of light absorbed by the sensor versus wavelength for the detector system.

Figure 20:
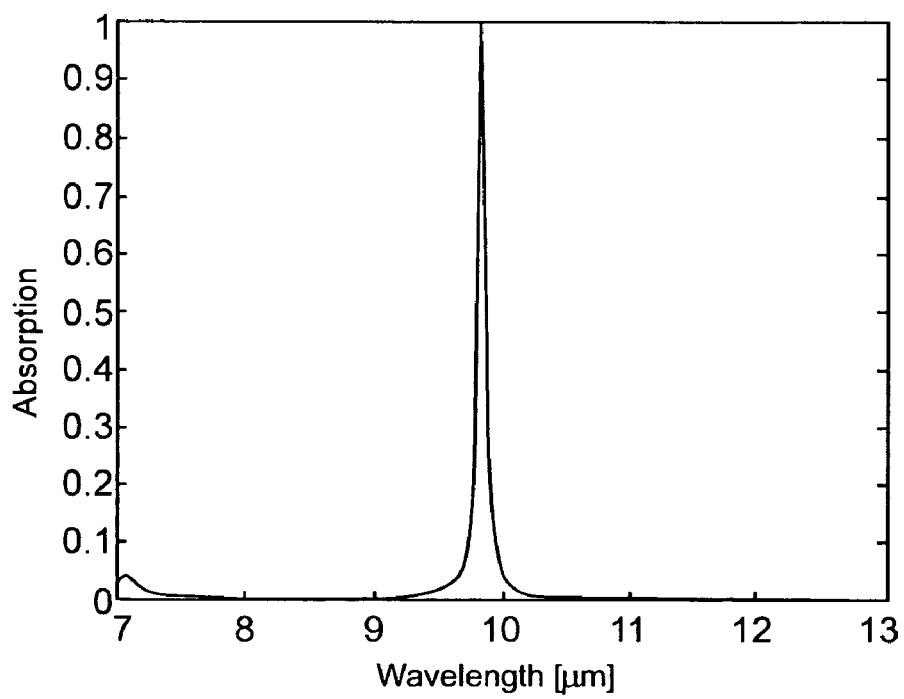
FIG. 20 is a graph of absorption versus wavelength for the resonant optical cavity of the table of FIG. 19.

The standing wave pattern has a minimum near the mirrors, however, so if the sensor is placed near the mirrors with an otherwise similar layer structure as shown in FIG. 19, the ZnS layer must have a much larger imaginary part of the index of refraction in order to achieve good coupling. The spectrum is shown in FIG. 20. When absorption layers are placed close to a mirror one is often better served by materials that are intrinsically highly absorbing in the IR such as Cr or Pd metal rather than relatively transparent semiconductors as it can be difficult or impossible to dope such materials highly enough to achieve such a large 'k'. On resonance, the coupling is still nearly 100% and, off-resonance, the absorption is still nearly zero. Both center-placed sensors and near-mirror-placed sensors can achieve detection beyond the traditional radiation limit with proper support and read-out design.

To quantify detector performance, noise in a thermal detector needs to be considered. Assume that the central plate of an optical cavity similar to that of FIG. 1 includes a resistor layer of Vanadium Oxide ($VO_x$) and is connected to the outside world by electrically conducting supports. Noise fluctuations can come from several sources, which include Johnson noise, 1/f noise, and thermal noise (both phonon and photon). Johnson noise originates from the interaction of charge carriers in a resistor with photons from the extreme long wave tail of the thermal emission distribution. The Johnson rms voltage noise takes the form:

$$\sqrt{\langle \Delta V^2 \rangle} = \sqrt{4kTRB}$$

where k is Boltzmann's constant, T is temperature, R is the resistance, and B is the bandwidth of the voltage measurement. To detect a signal, one must receive power that is approximately equal to the noise power. This is codified in a figure of merit called the noise equivalent power (NEP), which is defined as:

$$NEP = \frac{\langle \Delta V^2 \rangle}{\Re_V}$$

where $R_V$ is the detector responsivity in V/W. For a microbolometer sensor at peak responsivity frequencies, $R_V = \alpha V_b/G$, where α is the temperature coefficient of resistance (TCR), $V_b$ is the bias voltage, and G is the thermal conductance. If we assume a typical TCR of α=0.02/K, a microbolometer resistance of R=25 kΩ, and a readout bias of 0.2V applied for 250 μs once during every frame, then the room temperature Johnson noise limited NEP is 0.33 pW.

The second major noise source is 1/f noise. The origin of this noise is not well understood and is typically different from system to system. The 1/f rms voltage noise takes the form of:

$$\sqrt{\langle \Delta V^2 \rangle} = \sqrt{kV^2 \ln\frac{f_2}{f_1}}$$

where k is the 1/f noise parameter, $f_1$ is the time between recalibrations of a bolometer pixel (corresponding to the staring time or chopping time depending on which mode a bolometer is being used in), and $f_2$ corresponds to the bandwidth of the electrical readout ($f_2 \sim 1/\Delta t_{read}$). In the previous expression for Johnson noise, $B=f_2-f_1$. All other variables are the same as before. To calculate the 1/f noise-limited NEP, the previous parameters $f_1=30$ Hz, and $f_2=4$ kHz, and a typical $VO_x$ value for the 1/f noise parameter, $k=10^{-13}$ are used to get an NEP of 0.035 pW.

The most fundamental noise source is thermal conductance noise. Thermal conductance noise originates with the discreteness of the heat transfer to and from a highly isolated sensor. The discreteness can arise either from phonon fluctuations if conduction heat transfer dominates the system or photon fluctuations if radiation heat transfer dominates. In either case, the noise takes the form:

$$NEP = G\sqrt{\frac{kT^2}{C}}$$

where NEP is the noise equivalent power, G is the thermal conductance and C is the heat capacity of the sensor. (Assume a microbolometer bandwidth of B=¼τ where τ=C/G the time constant for the detector plate.) Radiation heat transfer is usually considered to be the ultimate limit of bolometer performance. In order to estimate the thermal conductance of a radiation-limited device, we differentiate the Stefan-Boltzmann radiation power law equation and obtain:

$$G_{rad} = 4(2A) \in \sigma T^3$$

If the size of a microbolometer sensor plate is 100 μm×100 μm, T=300 K, and the emissivity is 1, then $G_{rad}=1.5 \times 10^{-8}$ W/K. If the absorption of the sensor plate is dropped such that $\in = 0.01$, then $G_{rad} \sim 10^{-10}$ W/K, a value so low that radiation heat transfer will be overwhelmed by conduction fluctuations from the thermal supports.

The level to which the thermal conductance can be reduced depends on the resistance of the supports. For example, $G \sim 10^{-9}$ W/K can be achieved for high resistance supports. However, thermal conductances are not necessarily that low in current uncooled devices because other noise sources such as Johnson noise and the blackbody radiation limit are too high to make such low conductance useful.

Assuming that $G_{sup}$ is about $10^{-9}$ W/K. The noise equivalent power for a thermal conductance limited structure is NEP=0.38 pW. Summing the contributions from thermal, Johnson, and 1/f noise, the NEP=0.50 pW. This level of performance approaches that of the best cooled MCT detectors. If a single pixel is desired instead of an array (e.g. for a chemical detector application rather than imaging) even better performance can be obtained by using a high bolometer resistance. A 2.5 MΩ resistance allows a large resistance in the support arms, making $10^{-9}$ W/K achievable with current materials and standard supports. Read-out speed is sacrificed, however. The device would need to be read over an entire frame, for example, $f_2 \sim 60$ Hz and $f_1 \sim 30$ Hz. The Johnson noise and 1/f noise would be about the same or less while the bias voltage can be increased with less power dissipated into the device, improving the NEP.

Another important figure of merit of microbolometers is the detectivity D*, which normalizes the responsivity to the area and noise of the sensor.

$$D^* = R_v \sqrt{A} \frac{\sqrt{\Delta f}}{V_n},$$

where A is the effective area of the sensor under radiation, $V_n/\sqrt{\Delta f}$ is the total noise voltage per unit frequency bandwidth.

Figure 7:
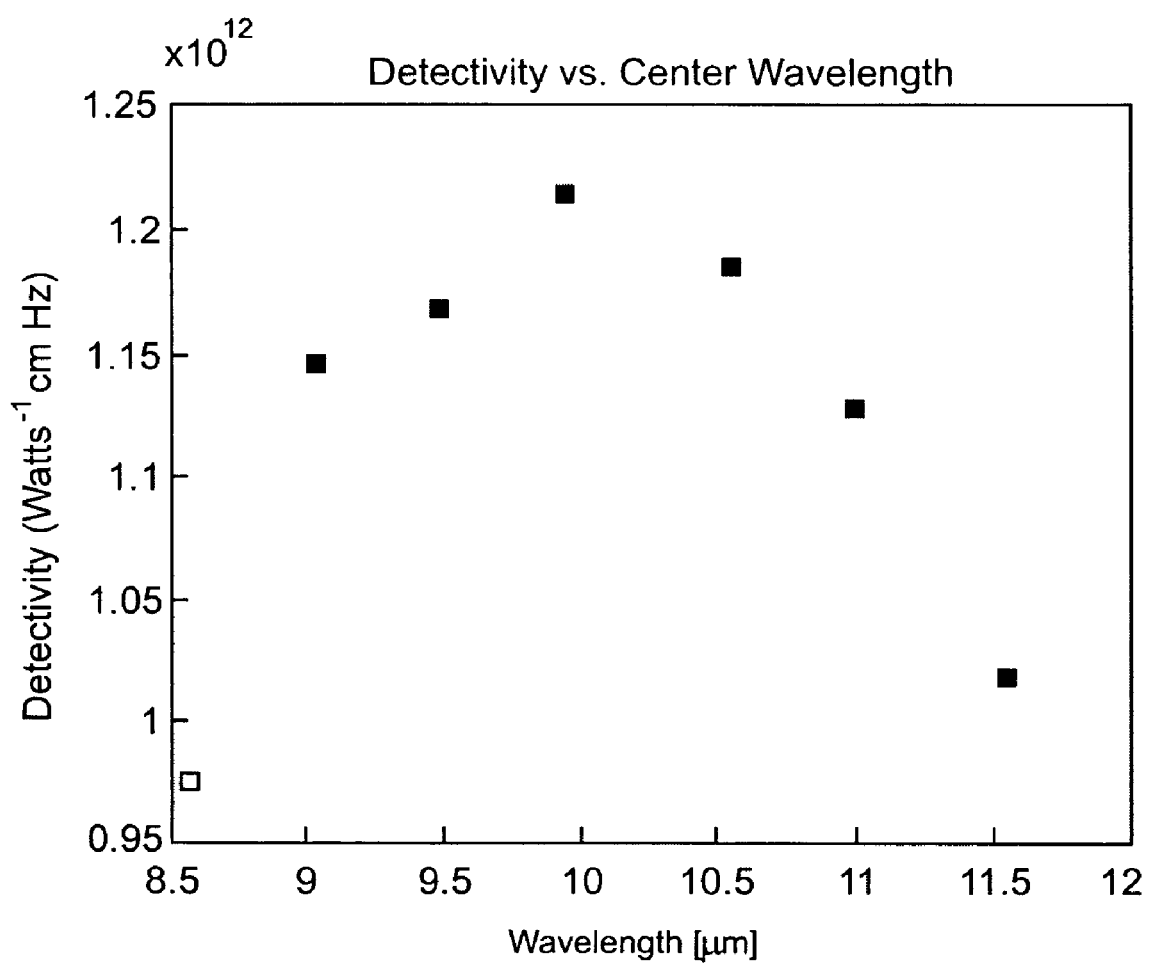
FIG. 7 is a graph of detectivity vs. wavelength for a thermal detector in accordance with the present invention having a chromium absorber layer inside an optical cavity optimized for ten microns.

For a radiation-limited thermal sensor, the standard fundamental detectivity limit is given by:

$$D^* = \frac{\varepsilon}{8\varepsilon(T_1^5 + T_2^5)^{\frac{1}{2}}}$$

where $\in$ is the emissivity, $T_1$ is the sensor temperature, and $T_2$ is the background temperature. However, this equation assumes an emissivity that is constant in both direction and wavelength. In FIG. 7 a simulation for a device in accordance with the present invention that is designed for a waveband somewhat larger ($\Delta v \sim 6$ cm$^{-1}$) than a standard atmospheric pressure broadened line ($\Delta v \sim 4$ cm$^{-1}$). Here the blackbody fluctuation equation has been integrated over solid angle with an emissivity of nearly one in the direction of an f/4 lens and a much lower emissivity in other directions. This corresponds to the case of a low absorption material placed in an optical cavity in accordance with the present invention whose spatial extent matches that of the lens. In addition, the spectral range of the optical cavity further reduces interaction with the background. On resonance, the optical cavity couples nearly 100% of the light into the sensor. Off resonance, the optical cavity rejects light back to the background and the mirrors themselves provide very little thermal light to the sensor by Kirchoff's Law so that a high reflectivity device has a very small emissivity. Mathematically, this means that one integrates Planck's Law (in the direction of the optical cavity) only over the spectral resonance band of the optical cavity. This leads to an NEP which goes as the square root of the spectral bandwidth. In reality, one multiplies Planck's Law by the cavity passband absorption but in the limit of narrow resonances, these two methods give similar results. The combination of spectral and spatial effects causes the radiation noise to plummet. FIG. 7 shows the detectivity of an ultrahigh sensitivity device that is radiation limited for a 6 cm$^{-1}$ resonance in the LWIR. An atmospheric line detector would have a somewhat higher detectivity because of its reduced spectral width.

The NEP of a sub-radiation limit sensor is far superior to that of a normal microbolometer with a filter, but its speed can be limited. The time constant of a microbolometer is $\tau=C/G$ where C is the heat capacity and G is the thermal conductance. Since reducing the thermal radiation limit reduces the thermal conductance, the heat capacity must be reduced in order to maintain $\tau$ at a normal frame rate of 30 Hz. This can be done by reducing the size of the pixel. Because the beam has to make multiple round trips of the cavity, there can be significant diffraction and coupling losses if the pixel size becomes comparable to the wavelength in a parallel plate cavity. There are a few ways to circumvent this problem. The simplest is to maintain pixel size but reduce the thickness of the bolometer membrane (sensor) to nanometer-scale thicknesses. This requires control of thin film stress but does not require a change in architecture. The second is to use a Gaussian optical cavity that is matched to produce a spot size that covers the bolometer membrane. The cavity focuses the light and thus the bolometer area can be significantly smaller. In such a design, diffraction will occur but the mirrors of the cavity are shaped (curved) to match the diffracted wavefront and redirect the diffracted wavefront back towards the bolometer membrane. This type of cavity is used in many lasers to match the beam size to the gain region. The mirrors can include stress-shaped mirrors, tunable mirrors, coated microlenses or the like. A third method of circumventing diffraction losses is to alter the bolometer membrane to become a sub-wavelength grating. This allows significant mass to be removed from the bolometer membrane without having to reduce the area and/or thickness of the bolometer membrane. The optical properties of sub-wavelength gratings can be altered for a desired amount of absorption in the same way as for reflection or transmission.

Any one or some combination of these may be used in sensor structures in accordance with the present invention. For example, assume a 10 micron bolometer membrane in a matched Gaussian cavity. If the thickness of the plate is 50 nanometers, and the system is made of normal materials such as silicon nitride, then the heat capacity will be on the order of $10^{-11}$ J/K, which if used with G of about $10^{-9}$ W/K, would maintain a time constant of $\tau=10$ ms. If the detector size were increased to 35 microns, the plate would preferably be thinned in some way or made into a grating.

One difficulty with achieving low thermal conductance in microbolometer supports is the need to maintain high electrical conductance. Simultaneously high electrical conductivity, $\sigma$, and low thermal conductivity, $\kappa$, is difficult to achieve and limited for conductors by the Wiedemann-Franz Law. Some of the materials with the highest ratio of $\sigma/\kappa$ are the thermoelectrics and some metal alloys such as NiFe. In the noise calculations set forth above, the resistance of a single-pixel bolometer was assumed to be 2.5 M$\Omega$. The supports for such a device could have a resistance up to about 100 k$\Omega$ or more per support before any significant loss in signal would be seen. Assuming a silicon dioxide support with a NiFe conductor (using relatively standard values for these materials), a 2 mm long beam with about a 0.55 μm$^2$ cross-sectional area would have a thermal conductance of $5\times10^{-10}$ W/K.

In a preferred embodiment of the present invention, an electrical (or optical) read-out operation occurs over the entire frame time to minimize bandwidth. If one wishes to sequentially read an entire row or column in an array during a single frame, say by using pulse bias, detection beyond the standard limit becomes more difficult. Because the electrical bandwidth increases, the Johnson noise increases, and the NEP degrades significantly. To avoid this, a smaller resistance plate can be used, say $R_{plate}$ of about 25 k$\Omega$ with supports of $R_{sup}\sim1$ k$\Omega$, but the achievable thermal conductance will be limited to a value on the order of $10^{-8}$ W/K for existing materials. There are a few ways to circumvent this problem; one technique is to create a thermal switch that only contacts the bolometer during electrical read-out. Thermal switches have been proposed and demonstrated in thermal detectors for chopping and responsivity control. Thermal switching to latch an electrical connection for thermal isolation during an electrical off cycle is used with thermoelectric coolers. The use of thermal switching to latch an electrical connection for thermal isolation during an electrical off cycle can be applied to microbolometers. The pixels are provided with extra leads, higher voltages, and voltage control circuitry. Stiction issues are addressed using a two-voltage-step actuation approach.

Figure 8:
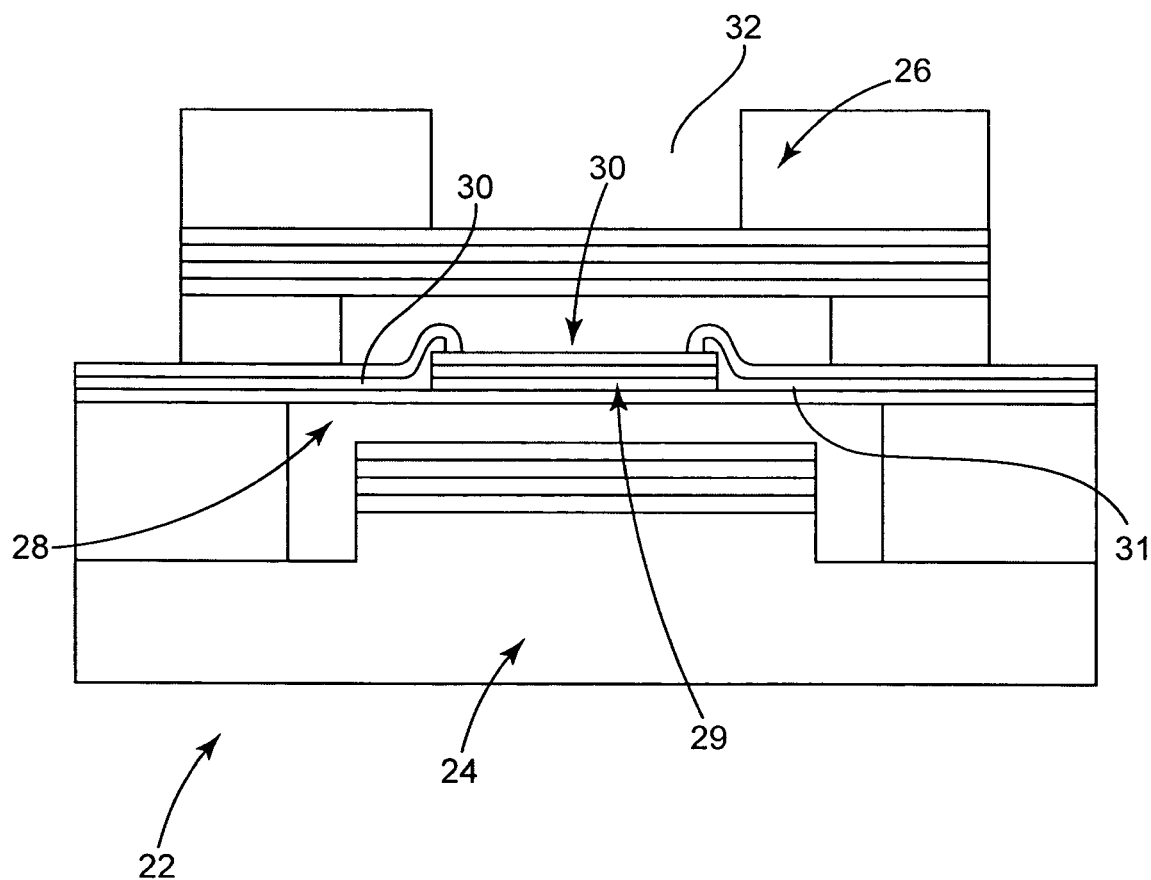
FIG. 8 is a schematic view of an exemplary thermal detector in accordance with the present invention.

An exemplary thermal detector 22 in accordance with the present invention is shown schematically in FIG. 8. Thermal detector 22, as shown, includes first mirror structure 24, second mirror structure 26, and sensor structure 28 supported within optical cavity 30 by support beams 30 and 31. Sensor structure 28 includes sensor portion 29 and support structures 30 and 31. Second mirror structure 26 includes aperture 32 that allows incoming radiation to pass through second mirror structure 26 and enter optical cavity 30.

Figure 9:
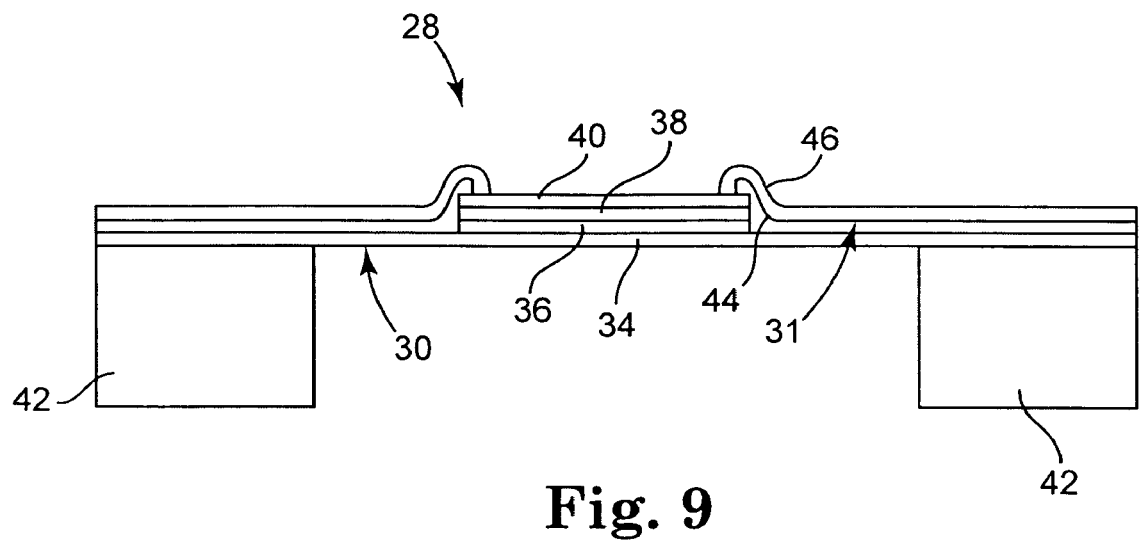
FIG. 9 is a schematic view of a sensor structure of the thermal detector of FIG. 8.
Figure 10:
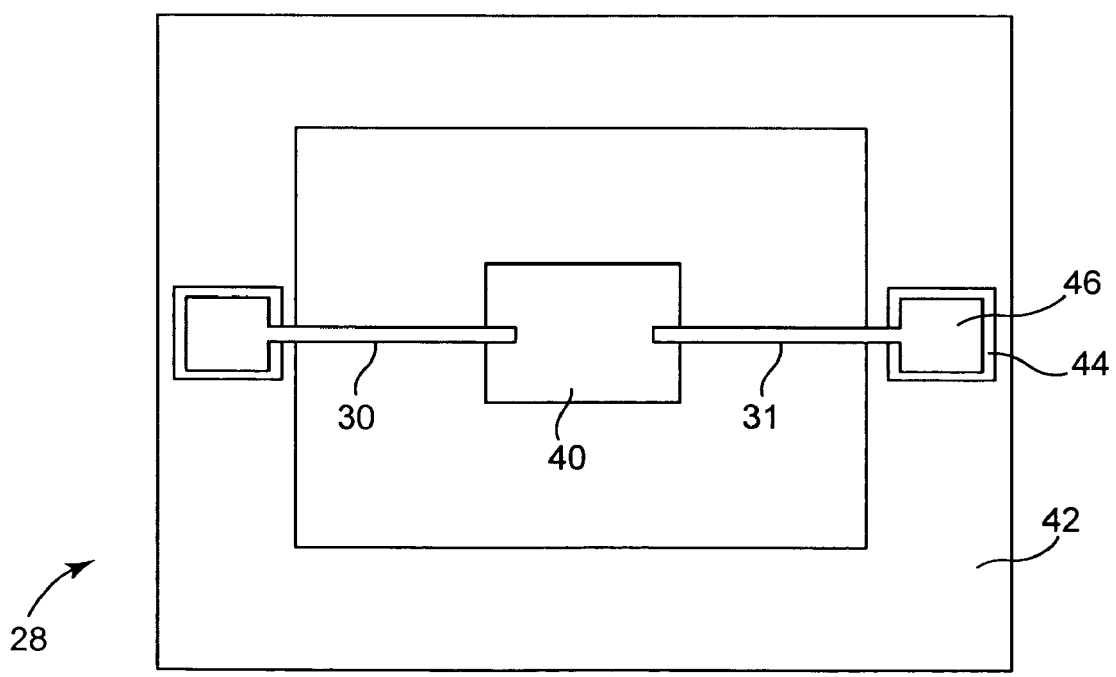
FIG. 10 is a top view of the thermal detector of FIG. 8.

An exemplary process for making thermal detector 22 preferably begins with three substrates. Known semiconductor processing techniques and MEMS fabrication techniques can be used to manufacture thermal detectors in accordance with the present invention. For process simplicity, a non-monolithic structure is illustrated and described. In some embodiments, one or more of the wafers can be eliminated by stacking more dielectrics. Silicon is chosen for its cost-effectiveness and widespread use, but other materials, such as germanium or quartz can be used as well depending on process and wavelength considerations. An exemplary sensor structure 28 is shown in FIG. 9 in cross-section and a top view is shown in FIG. 10. Sensor structure 28 includes sensor portion 29 and support structures 30 and 31. The sensor structure 28 includes a first dielectric layer 34, an absorbing layer 36, a second dielectric layer 38, a TCR (sensor) layer 40, and substrate 42. Some or all of these layers could be removed, combined (e.g. a common layer for sensor and absorption, or dielectric and absorption), or added to (e.g. a protective dielectric could be put over the TCR material). It is assumed in the exemplary process that the sensor and absorber layers are uniform across the device. However in some alternatives, the sensor and absorber can be patterned so long as the combined emissivity of the combined sensor/absorber structure is specifically designed to be less than the standard blackbody radiation limit and is absorption-coupled to the optical cavity in the direction of the optical signal (while not being optimally coupled in most or all other directions). In one example, the dielectric material is silicon dioxide which also functions as the absorber, while the TCR material is vanadium oxide (VOx). The VOx has been chosen because it is a current industry standard, but any number of other TCR materials can be used. The sensor is patterned and then support layers are deposited and patterned. The supports are designed to have very low thermal conductance and, in the illustrated embodiment, a first layer 44 of silicon dioxide and second layer 46 of NiFe are provided on layer 34 used as the structural and electrically-conductive layers respectively for support beams 30 and 31. Two support beams are illustrated but any of support beams such as one (with two NiFe lines) or three or four (where one or more are $SiO_2$ only) can be used.

Once the sensor and supports are complete, the substrate underneath the device region is etched away by wet or dry etching, for example by a conventionally known Bosch process. The removal of the portion of the substrate beneath the sensor in this embodiment prevents unwanted reflections and silicon absorption. If these processes require etch stop or protective layers, then these can be added to the device depositions above. The Bosch process, for example, may only need the $SiO_2$ dielectric as an etch stop.

Figure 11:
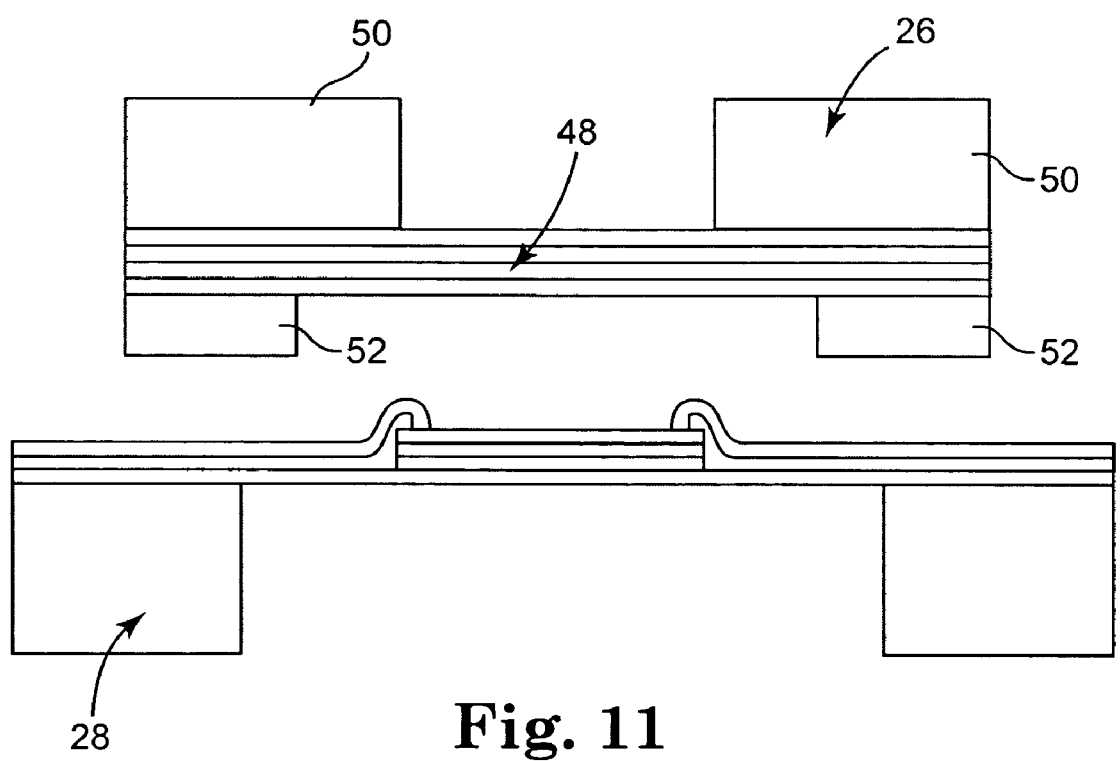
FIG. 11 is a partial exploded view of the thermal detector of FIG. 8 showing a mirror structure and sensor structure.

Referring to FIG. 11, second mirror structure 26 and sensor structure 28 are shown in exploded view. Second mirror structure 26 includes distributed Bragg reflector (DBR) structure 48 deposited on a substrate 50 along with spacer(s) 52 of appropriate thickness. The spacer(s) 52 are patterned to surround the device region of the sensor structure 28 while still allowing access to the electrical leads of the sensor structure 28. The DBR structure 48 may include, for example, Ge and ZnS quarter-wavelength layers. It should be noted that for some devices, better spectral characteristics (e.g. improved symmetry in an absorption versus frequency plot) might be obtained by using non-quarter wave layers. The spacer(s) 52 can be bonded to the substrate 50 using any one of a number of semiconductor processes, for example, thin epoxy. The spacer(s) 52 are used to define a desired distance between the second mirror structure 26 and the sensor. In most cases the spacing is used to help define an overall half-wavelength or multiple-of-a-half-wavelength optical resonant cavity. As noted above, the substrate underneath the device region is preferably removed by a wet or dry etch (for example the Bosch process, which would require an extra $SiO_2$ etch-stop layer and its subsequent removal) to eliminate substrate reflections and absorption.

Figure 12:
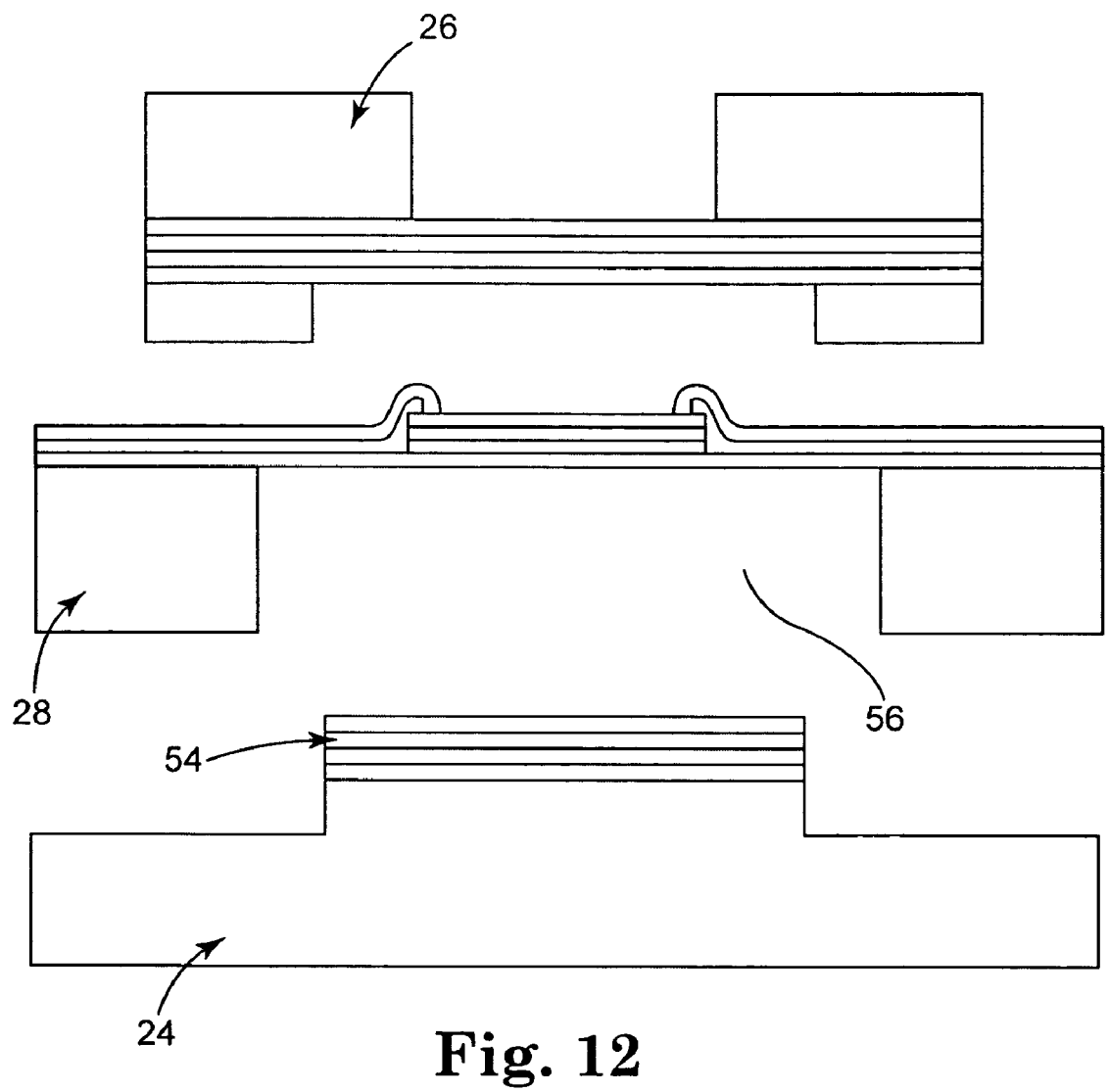
FIG. 12 is an exploded view of the thermal detector of FIG. 8 showing first and second mirror structures and a sensor structure.

The first mirror structure 24 shown in FIG. 12 is also preferably coated with a DBR 54 or similar high-reflectivity coating. In many cases, the reflectivity of the first mirror structure 24 will be chosen to be nearly 100% to minimize losses, minimize unwanted coupling to directions other than that of the signal, and extend the useful tuning bandwidth in the case of tunable devices. DBR 54 is preferably patterned and the substrate region around it is over-etched to a predetermined depth. The first mirror structure 24 can then be inserted into a corresponding region 56 underneath the sensor structure 28 so that the first mirror structure 24 and sensor structure 28 are at a well-defined spacing. Again, this spacing is preferably chosen to define an overall cavity length (including all structures) of a half-wavelength or multiple-of-a-half-wavelength of the desired resonant frequency (or starting resonant frequency in the case of tunable devices).

In a thermal detector, the top mirror and sensor layer can be combined and still have performance beyond the radiation noise limit. This requires that the absorber and sensor combination be specifically designed for low emissivity compared to the blackbody radiation limit for the area of the device and that the supports and read-out be designed to reduce other noise sources below the blackbody radiation limit. Such an architecture is described in U.S. patent application Ser. No. 11/805,240 to Talghader et al., and would look similar to the devices described therein except with the supports and read-out designed for much lower noise. However, there are performance aspects related to this. First, the extra volume of the top mirror when combined with the absorber/sensor may increase the time constant. Methods to mitigate this, such as by thinning the top mirror by using special metals and dielectrics as described in U.S. patent application Ser. No. 11/805,240, may result is less optimal absorption characteristics off axis and off-resonance. Second, the two-layer optical cavity may allow more light from directions other that the optical axis, possibly reducing efficiency. That being said, significant NEP improvement can still be achieved.

As noted previously, the sensor plate itself can be placed at a variety of points within the optical cavity, depending on the optical coating design. For example, if the sensor is equidistant between the two mirrors, a lightly doped semiconductor layer may work well as the absorber and/or TCR material. If the sensor plate is close to the top or bottom mirrors, a thin metal layer may work well for optimal coupling.

Figure 13:
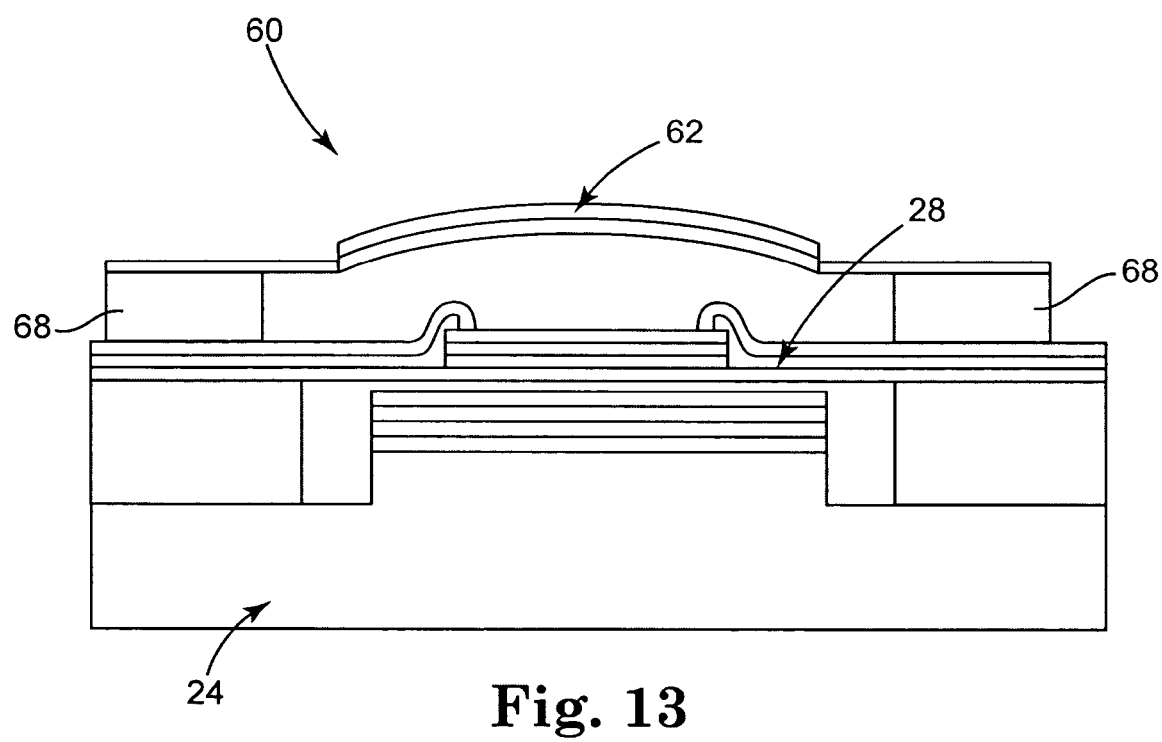
FIG. 13 is a schematic view of another exemplary thermal detector in accordance with the present invention.

A case of particular interest is when the sensor is near the flat bottom mirror and the cavity has a curved top mirror as shown in thermal detector 60 of FIG. 13. Thermal detector 60 is similar to thermal detector 22 shown in FIG. 8 and includes first mirror structure 24, sensor structure 28, second mirror 62, respectively, and spacers 68. Second mirror structure 28 may comprise any layered mirror structure such as those described herein. In this case, if the curvature of the second mirror structure 62 is set to form a half-spherical cavity with the flat first mirror structure 24 (i.e. the radius of curvature of the second mirror structure 62 matches the distance between the first and second mirror structures, 24 and 62, respectively) then lower f/# optics may be matched to the optical cavity than are otherwise possible with flat mirror cavities. A normal flat-flat mirror cavity that is sensing a standard atmospheric chemical line of spectral width 4 $cm^{-1}$ might use an f/4 lens at best before the angular range of the input signal begins to significantly degrade the spectral resolution of the sensor. The usable f/# and therefore the NEP can be lowered significantly by matching the angular spread of the rays (i.e. the shape of the wavefront) through the lens to the radius of curvature of the second mirror structure 62. The placement of the sensor near the first mirror structure 24 insures that the over all propagation distance of any ray in the cavity is nearly the same. More particularly, the sensor is spaced from first mirror structure 24 by a distance corresponding a small fraction of a wavelength, for example, less than $\lambda/10$. The use of the curved mirror, low f/# optics, and proper sensor placement allows the sensor to be reduced in size relative to the resonant wavelength as compared to flat-flat mirror cavities.

Figure 14:
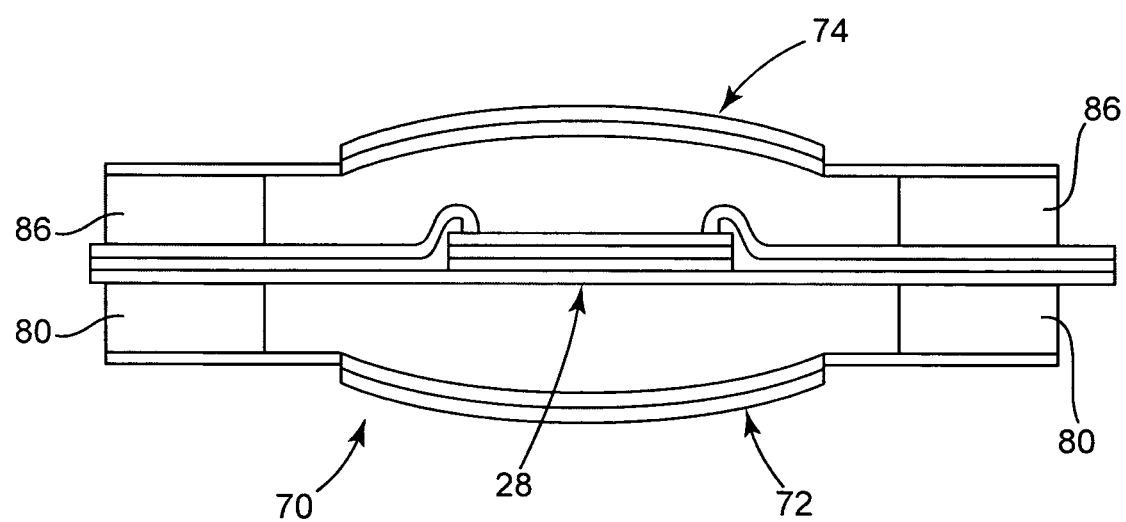
FIG. 14 is a schematic view of another exemplary thermal detector in accordance with the present invention.

In FIG. 14 another exemplary thermal detector 70 in accordance with the present invention is schematically shown. Thermal detector 70 includes first and second mirror structures, 72 and 74, respectively, and sensor structure 28. First mirror structure 72 comprises multilayer stack 76 and spacers 80. Second mirror structure 74 comprises multilayer stack 82 and spacers 86. The performance of the curved-curved cavity is relatively similar to the curved-flat cavity except for an increased minimum length, which may introduce other resonances into the spectral bands of the DBR mirrors. Such a mirror can be used to simplify manufacturing processes as the top and bottom mirrors could be nearly identical in optics and electrode structure and thus diced from the same wafers.

Figure 15:
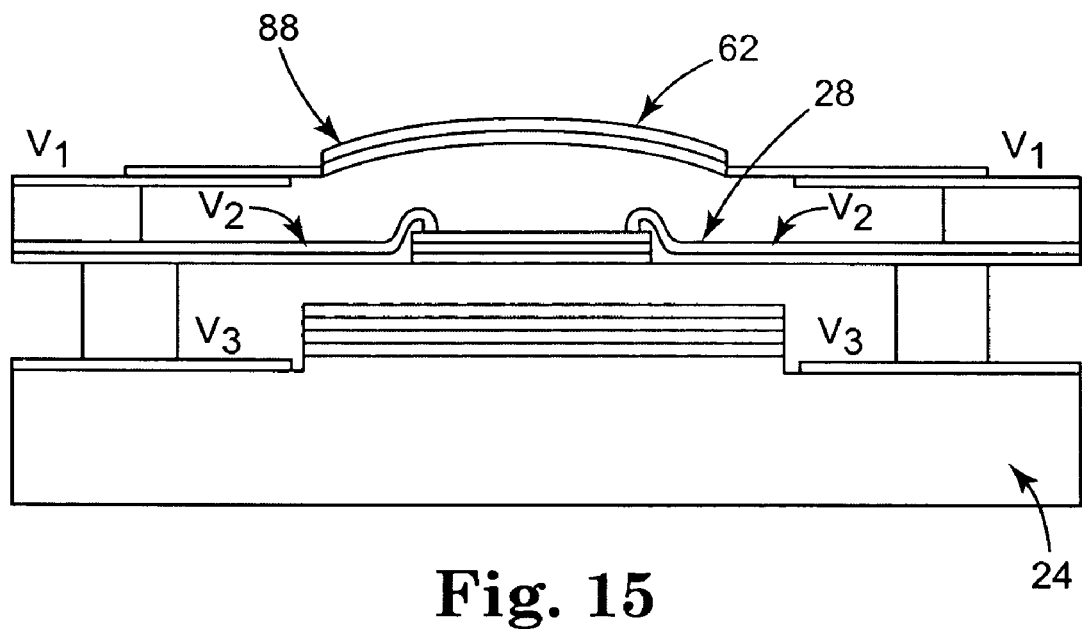
FIG. 15 is a schematic view of another exemplary thermal detector in accordance with the present invention.
Figure 16:
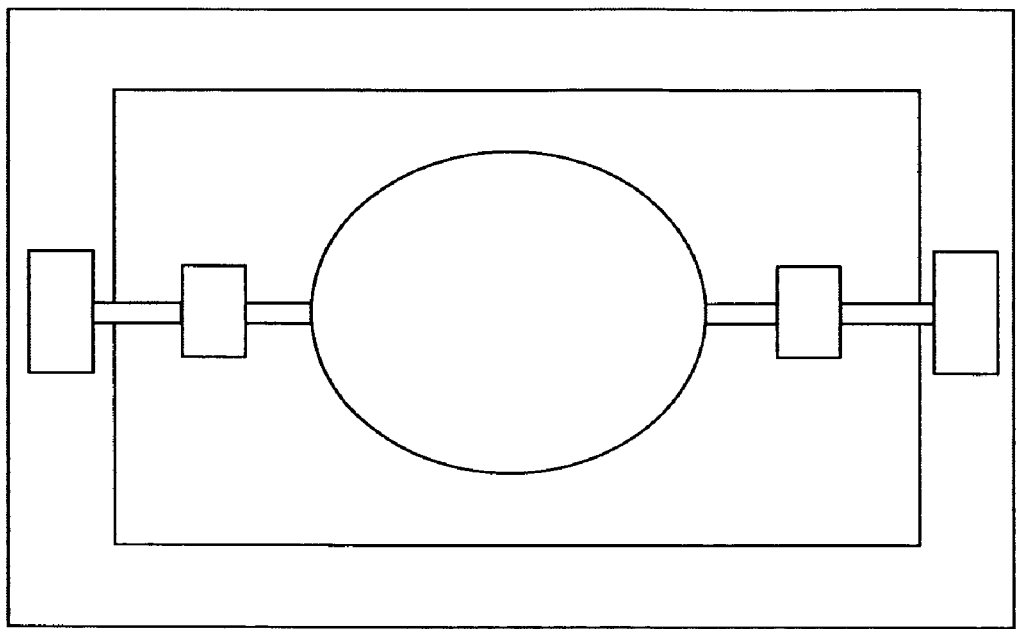
FIG. 16 is a top view of the thermal detector of FIG. 15.
Figure 17:
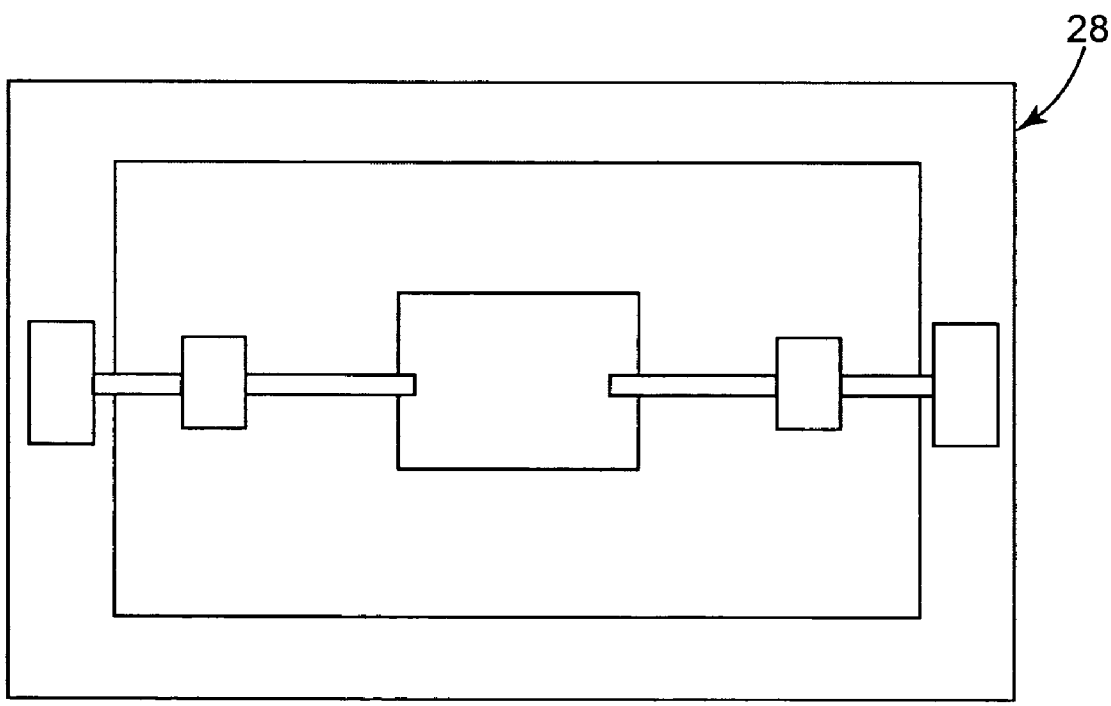
FIG. 17 is a top view of a sensor structure of the thermal detector of FIG. 15.

Thermal detectors in accordance with the present invention can also be made tunable. This can be done in many ways with many types of micromechanical actuators, such as piezoelectric, electrostatic, and magnetic for example. An exemplary electrostatic based thermal detector 88 in accordance with the present invention is shown in FIG. 15 and is similar to the thermal detector 60 shown in FIG. 13. FIG. 16 shows a top view of detector 88 and FIG. 17 shows a top view of sensor structure 28. The process remains largely the same but would include extra steps for patterning actuators and supports for the top mirror. Actuation electrodes provided on the supports are optional. The actuator voltage V2 could be applied directly to the sensor element as shown or with separate electrodes. If applied directly to the TCR layer and/or absorber layers then the read-out bias would need to be considered in applying voltages. For example, if the actuation voltages (V1−V2)=(V3−V2)=20 V but 0.02 V were required to bias the device for read, then one side of V2 would be set at 0 V and the other would be set at 0.02 V, while V1 and V3 would be set at 20 V. The potential differences V1−V2 and V3−V2 are not in general the same, and their magnitude and timing can be adjusted individually to maintain optimal spectral characteristics. These actuation voltages may also be either applied continuously or dynamically (e.g. timed steps or pulses). In certain cases, layers in the top and bottom mirrors and the sensor may be used as actuation electrodes. For example, the surface Ge layer facing the gap in the mirrors and the TCR layer in the sensor can be used as actuation electrodes.

In most cases, case, it is preferable that dielectric not come between electrodes as this may lead to undesired dielectric charging. Regions of the sensor structure may also have a metal electrode underneath the dielectric that may be directly connected to the sensor top actuation electrode. Also note that in order to read-out the detector, a potential difference will need to be placed across the left and right electrodes of the sensor. This can cause a slight tilt in the position of the detector relative to the top and bottom mirrors. However, the potential difference will likely be very small relative to the actuation voltages and therefore the tilt will not affect optical performance except at extremely high cavity finesse.

Although it is expected that most applications of detection beyond the radiation limit will be for uncooled thermal devices in the infrared, the concept can equally well be applied to photon detectors in the infrared. Fundamentally the present invention reduces the interaction of the thermal background with narrowband detectors, so any detector that is background limited can use the concepts herein. In a photon detector, one will usually cool the detector to a level where the limiting noise is the thermal background. If one designs the electron-hole absorbing region of the detector to have a small absorption per pass and places this system in the cavity, the background limit is reduced. Therefore in order to retain background-limited performance, one would have to further cool the device so that the device noise is below the new background limit. Under normal circumstances, this process is little different from a standard cold-shielded and cold-filtered detector, but with the development of microcoolers that can cool very small volumes, one could encounter electron-hole generation regions that are cooled to temperatures much smaller than the system around them. (Or alternatively the regions around them become heated in some way.) This type of photon detector could certainly benefit from the techniques described here.

Figure 18:
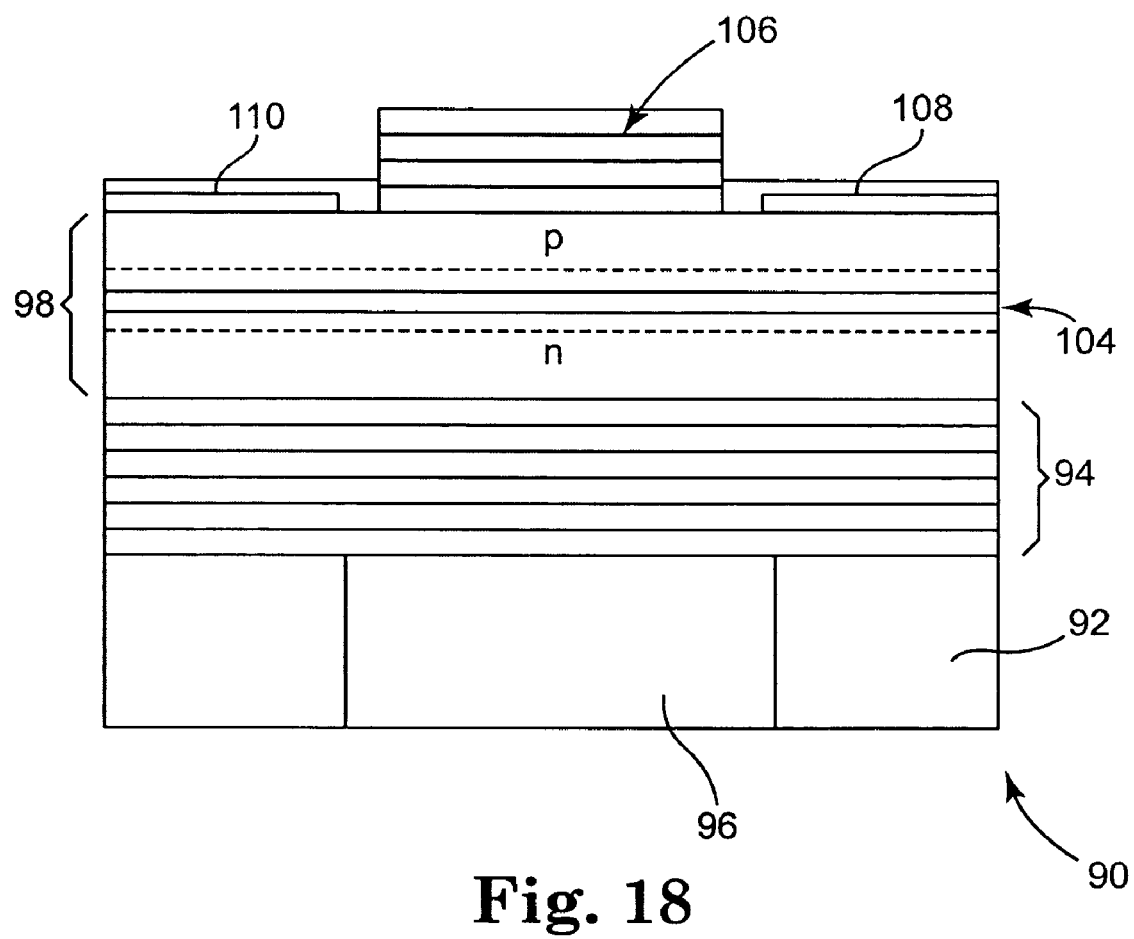
FIG. 18 is a schematic view of an exemplary photon detector in accordance with the present invention.

An exemplary photon detector 90 in accordance with the present invention is schematically shown in FIG. 18. Detector 90 includes substrate 92 having first mirror structure 94 and optional microcooler 96. Active region 98 is provided on first mirror structure 94. Active region 98 comprises n-type layer 100 and p-type layer 102 having interface region 104 therebetween. Interface region comprises a low bandgap absorbing electron-hole generation region. Photon detector 90 also includes second mirror structure 106 and first and second contacts, 108 and 110. The sensor in this embodiment includes the absorbing electron-hole generation region 104. The optical cavity include the region between mirrors 94 and 106 and including mirrors 94 and 106. Photon detector 90 operates in much the same manner as a normal photodetector in that infrared light is absorbed by the electron-hole-pair generation region 104, except in this device, only light on the cavity resonance is significantly absorbed. In this device, the region around the sensor is preferably cooler than the surrounding components and thus a reduced absorption in the cavity leads to a reduced radiation limit. Photon detector 90 can be made tunable by introducing a gap and electrodes between one mirror and the remainder of the device.

Thermal detectors in accordance with the present invention can be used in chemical sensing devices, industrial process control devices, engine monitoring devices, effluent monitoring devices, environmental monitoring devices, temperature measurement devices, pressure measurement devices, explosives detection devices, imaging devices, medical monitoring devices, for example. Such detectors may, for example, replace any filter and infrared detector, monochromator and infrared detector, or grating/diffractive structure and infrared detector in such systems. The operational concept for these applications is that emission/absorption spectra being read has variations in its spectral intensity that can be measured using detectors in accordance with the present invention and converted into a relevant signal that, for example, describes intensity, intensity ratio, or linewidth to assess chemical concentration, temperature, or pressure.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

REFERENCES

The following references are each incorporated by reference herein for their entire disclosure and for all purposes.

1. K. Lai and J. C. Campbell, "Design of a tunable GaAs/AlGaAs multiple-quantum-well resonant-cavity photodetector," *IEEE Journal of Quantum Electronics*, vol. 30, no. 1, pp. 108-14, 1994.
2. M. S. Wu, E. C. Vail, G. S. Li, W. Yuen, and C. J. Chang-Hasnain, "Widely and continuously tunable micromachined resonant cavity detector with wavelength tracking," *IEEE Photonics Technology Letters*, vol. 8, no. 1, pp. 98-100, 1996.
3. Y. Wang, B. J. Potter, and J. J. Talghader, "Coupled absorption filters for thermal detectors," *Optics Letters*, vol. 31, no. 13, pp. 1945-1947, Jul. 1, 2006.
4. H. Y. Fan, "Effects of free carriers on the optical properties," in *Semiconductors and Semimetals*, vol. 3, ed. R. K. Willardson and A. C. Beer, pp. 405-419, 1967.
5. F. L. Pedrotti and L. S. Pedrotti, *Introduction to Optics*, Prentice Hall, p. 573, 1993.
6. E. Palik, *Handbook of Optical Constants*, Academic Press, 1998.

7. J. I. Pankove, *Optical Processes in Semiconductors*, Dover, pp. 74-76, 1971.
8. C. Kittel and H. Kroemer, *Thermal Physics, 2nd Ed.*, Freeman, 1980.
9. R. A. Wood, "Monolithic silicon microbolometer arrays," in *Semiconductor and Semimetals*, Eds. P. W. Kruse and D. D. Skatrud, vol. 47, pp. 43-121.
10. W. Liu and J. J. Talghader, "Current-controlled curvature of coated micromirrors," *Optics Letters*, vol. 28, no. 11, pp. 932-934, Jun. 1, 2003.
11. K. Cao, W. Liu, and J. J. Talghader, "Curvature compensation in micromirrors with high reflectivity optical coatings," *IEEE Journal of Microelectromechanical Systems*, vol. 10, no. 3, pp. 409-417, September 2001.
12. S. Collin, F. Pardo, R. Teissier, and J. L. Pelouard, "Efficient light absorption in metal-semiconductor-metal nanostructures," *Applied Physics Letters*, vol. 85, no. 2, pp. 194-196, 2004.
13. C. M. Hanson, D. Dudley, and J. E. Robinson, "Thermal imaging system with integrated thermal chopper," U.S. Pat. No. 5,486,698 (23 Jan. 1996).
14. W. B. Song and J. J. Talghader, "Adjustable responsivity for thermal infrared detectors," *Applied Physics Letters*, vol. 81, pp. 550-552, 2002.
15. C. Hilbert, R. Nelson, J. Reed, B. Lunceford, A. Somadder, K. Hu, and U. Ghoshal, "Thermoelectric MEMS coolers," *Proceedings of the International Conference on Thermoelectrics*. pp. 117-122, 1999.
16. T. S. Kim and H. C. Lee, "A highly sensitive bolometer structure with an electrostatic-actuated signal bridge," *Transactions on Electron Devices*, vol. 53, no. 9, pp. 2392-2400, 2006.
17. Y. Wang and J. J. Talghader, "Stiction-free soft landing for infrared thermal detectors," Technical Digest of the 2006 IEEE/LEOS Optical MEMS Conference, Big Sky, Mont., Aug. 21-24, 2006, pp. 60-61.
18. D. A. Czaplewski, H. Sumali, J. E. Massad, J. D. Kuppers, I. Reines, W. D. Cowan and C. P. Tigges, "A soft-landing waveform for actuation of a single-pole single-throw Ohmic RF MEMS switch," J., Microelectromech Syst., vol. 15, pp. 1586-1594, 2006.

What is claimed is:

1. A thermal detector for sensing infrared radiation, the thermal detector comprising:
    a resonant optical cavity at least partially defined by first and second spaced apart layered thin-film mirror structures; and
    an infrared sensor operatively positioned between the first and second thin-film mirror structures and suspended within the resonant optical cavity by one or more support beams so radiation received by the resonant optical cavity impinges on at least a surface portion of the infrared sensor, wherein the infrared sensor is absorption coupled with the resonant optical cavity and the absorption of the infrared sensor varies with direction and wavelength.

2. The thermal detector of claim 1, wherein at least one of the first and second thin-film mirror structures comprises a Distributed Bragg Reflector.

3. The thermal detector of claim 1, wherein the first and second thin-film mirror structures provide a standing maximum centered in the resonant optical cavity.

4. The thermal detector of claim 1, wherein at least one of the first and second thin-film mirror structures comprises a reflectivity centered at about ten microns.

5. The thermal detector of claim 1, wherein the resonant optical cavity provides a vacuum to thermally isolate the infrared sensor from the first and second thin-film mirror structures.

6. The thermal detector of claim 1, wherein the infrared sensor comprises a bolometer.

7. The thermal detector of claim 6, wherein the bolometer comprises a thin-film temperature sensitive resistor connected to the one or more support beams.

8. The thermal detector of claim 7, wherein the thin-film temperature sensitive resistor comprises one or more of vanadium oxide, YBaCuO, polysilicon, and titanium.

9. The thermal detector of claim 1, wherein the one or more support beams comprise one or more electrically conducting support beams and wherein the one or more electrically conducting support beams thermally isolate the infrared sensor and comprises a thermal conductance per unit surface area below the black body radiation limit of about 1 W/(Km$^2$).

10. The thermal detector of claim 1 in combination with one or more of a chemical sensing device, an industrial process control device, an engine monitoring device, an effluent monitoring device, an environmental monitoring device, a temperature measurement device, a pressure measurement device, an explosives detection device, an imaging device, and a medical monitoring device.

11. A thermal detector for sensing infrared radiation, the thermal detector comprising:
    a resonant optical cavity at least partially defined by first and second spaced apart layered thin-film mirror structures, the optical cavity having an optical axis and resonant wavelength; and
    an infrared sensor operatively positioned between the first and second thin-film mirror structures and suspended within the resonant optical cavity by one or more support beams so radiation received by the resonant optical cavity impinges on at least a surface portion of the infrared sensor, wherein the at least a surface portion of the infrared sensor is absorption coupled with the resonant optical cavity, the absorption of the at least a portion of the infrared sensor varies with direction and wavelength, and wherein the at least a surface portion of the infrared sensor has an absorption less than or equal to twenty-five percent along directions other than the optical axis and at wavelengths other than the resonance wavelength.

12. The thermal detector of claim 11, wherein the infrared sensor has an absorption less than about ten percent.

13. The thermal detector of claim 11, wherein the infrared sensor comprises a bolometer.

14. The thermal detector of claim 11, wherein the one or more support beams comprise one or more electrically conducting support beams and wherein the one or more electrically conducting support beams thermally isolate the infrared sensor and comprises a thermal conductance per unit surface area below about 1 W/K/m$^2$.

15. The thermal detector of claim 11, wherein the infrared sensor comprises a membrane having a thickness less than about one hundred nanometers.

16. The thermal detector of claim 11, wherein the one or more support beams comprises a thin-film structure comprising an insulating layer and an electrically conductive layer.

17. A method of sensing infrared radiation, the method comprising the steps of:
    providing a resonant optical cavity at least partially defined by first and second spaced apart thin-film mirror structures and an infrared sensor suspended within the resonant optical cavity;

causing radiation to enter the resonant optical cavity and absorption couple with the infrared sensor wherein absorption of radiation by the infrared sensor varies with direction and wavelength; and measuring a change in the infrared sensor caused by the radiation coupled with the infrared sensor.

18. The method of claim 17, therein the infrared sensor comprises a bolometer.

19. The method of claim 17, wherein the step of measuring a change in the infrared sensor includes measuring a change in the resistance of at least a portion of the infrared sensor.

20. A method of making a thermal detector for sensing infrared radiation, the method comprising the steps of:

forming a resonant optical cavity at least partially defined by first and second spaced apart thin-film mirror structures;

suspending an infrared sensor within the resonant optical cavity; and positioning the infrared sensor within the optical cavity so the infrared sensor is absorption coupled with the resonant optical cavity, the absorption of the infrared sensor varies with direction and wavelength, and the absorption of the resonant wavelength of the optical cavity by the sensor is greater than twenty-five percent.

21. The method of claim 20, comprising providing a vacuum in the resonant optical cavity.

22. The method of claim 20, wherein the step of suspending an infrared sensor within the resonant optical cavity comprises forming a bolometer structure.

23. The method of claim 20, wherein the absorption of the resonant wavelength of the optical cavity by the sensor is greater than seventy-five percent.

24. A thermal detector for sensing infrared radiation, the thermal detector comprising:

a resonant optical cavity at least partially defined by first and second spaced apart layered thin-film mirrors and having an optical axis; and an infrared sensor operatively positioned between the first and second thin-film mirrors, the infrared sensor comprising associated physically attached structure wherein the emissivity of the infrared sensor and the physically attached structure is larger by interference along the direction of the optical axis than other directions so the infrared sensor heat transfer is reduced compared to a blackbody.

25. The thermal detector of claim 24, wherein the infrared sensor is integrated with one of the first and second thin-film mirrors.

26. The thermal detector of claim 24, wherein the infrared sensor is read-out optically using one or more of a change in optical constants, shape, and position.

27. The thermal detector of claim 24, wherein the infrared sensor comprises one or both of electrically conducting supports and an electronic sensor.

28. The thermal detector of claim 24, wherein the infrared sensor comprises one or both of electrically conducting supports and a bolometer.

29. The thermal detector of claim 24, wherein the infrared sensor comprises one or both of electrically conducting supports and a Shottky barrier.

30. The thermal detector of claim 24, wherein the infrared sensor comprises one or both of electrically conducting supports and a diode.

* * * * *